(12) United States Patent
Kinney et al.

(10) Patent No.: US 7,351,711 B2
(45) Date of Patent: Apr. 1, 2008

(54) TRICYCLIC INDANYLS AS INTEGRIN INHIBITORS

(75) Inventors: William A. Kinney, Newtown, PA (US); Diane K. Luci, Horsham, PA (US); Bruce E. Maryanoff, Forest Grove, PA (US)

(73) Assignee: Janssen Pharmaceutical, N.V., Beerse (BE)

( * ) Notice: Subject to any disclaimer, the term of this patent is extended or adjusted under 35 U.S.C. 154(b) by 352 days.

(21) Appl. No.: 10/900,764

(22) Filed: Jul. 28, 2004

(65) Prior Publication Data

US 2005/0026917 A1 Feb. 3, 2005

Related U.S. Application Data

(60) Provisional application No. 60/491,629, filed on Jul. 31, 2003.

(51) Int. Cl.
*C07D 401/12* (2006.01)
*C07D 471/04* (2006.01)
*A61K 31/435* (2006.01)

(52) U.S. Cl. ............. 514/275; 514/290; 514/300; 544/330; 544/331; 546/111; 546/122

(58) Field of Classification Search ............. 544/330, 544/331; 546/111, 122; 514/275, 290, 300
See application file for complete search history.

(56) References Cited

U.S. PATENT DOCUMENTS

| | | | |
|---|---|---|---|
| 3,462,443 A | 8/1969 | Paragamian | |
| 5,474,765 A | 12/1995 | Thorpe | |
| 5,762,918 A | 6/1998 | Thorpe | |
| 2002/0016625 A1 | 2/2002 | Falotico et al. | |

FOREIGN PATENT DOCUMENTS

| | | |
|---|---|---|
| WO | WO 96/32907 | 10/1996 |
| WO | WO 01/96334 | 12/2001 |
| WO | WO 2004/020435 | 3/2004 |

OTHER PUBLICATIONS

Agrez et al., The alpha-v-beta-6 Integrin induces gelatinase B secretion in colon cancer cells, Int. J. Cancer, 81, pp. 90-97, 1999.*
Brooks et al., Integrin alpha-v-beta-3: A therapeutic target, DN&P, 10(8), pp. 456-461, Oct. 1997.*
Gladson et al., Vitronectin Expression in Differentiating Neuroblastic Tumors, American Journal of Pathology, vol. 150, No. 5, pp. 1631-1646, May 1997.*
Kim et al., Vitronectin-driven Human Keratinocyte Locomotion Is Mediated by the alpha-v-beta-5 Integrin Receptor, The Journal of Biological Chemistry, vol. 269, No. 43, pp. 26928-26932, Oct. 1994.*
Nip et al., The role of the Integrin vitronectin receptor, alpha-v-beta-3 in melanoma metastasis, Cancer and Metastasis Reviews, 14, pp. 241-252, 1995.*

Raynal et al., Bone Sialoprotein Stimulates in vitro Bone Resorption, Endocrinology, vol. 137, No. 6, pp. 2347-2354, 1996.*
Schvartz et al., Vitronectin, The International Journal of Biochemistry & Cell Biology, 31, pp. 539-544, 1999.*
Simone, Oncology: Introduction, Cecil Textbook of Medicine, 20th Edition, vol. 1, pp. 1004-1010, 1996.*
Antonov et al., Medline Abstract (American Journal of Pathology, vol. 165, Issue 1, pp. 247-258) Jul. 2004.*
Ulrich, Chapter 4: Crystallization, Kirk-Othmer Encyclopedia of Chemical Technology, Aug. 2002.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Peterson et al., Expanding the Scope of Crystal Form Evaluation in Pharmaceutical Science, J Pharm Pharmaceut Sci, 9(3), pp. 317-326, 2006.*
European Search Report, dated Dec. 2, 2004, for European Appln. No. EP 0425 4584.
Luci, Diane K. et al., "A Concise Synthesis of an Indenopyrrolididine-Based DUal alphaVbeta3/5 Integrin Antagonist", Heterocycles, vol. 62, Nov. 7, 2003.
Miller, William H. et al., "Orally Bioavailable Nonpeptide Vitronectin Receptor Antagonists with Efficacy in an Osteoporosis Model", Bioorg. Med. Chem. Lett., vol. 9, 1999, pp. 1807-1812.
Gould, Philip L., "Salt selection for basic drugs", International Journal of Pharmaceutics, 1986, 201-217, 33, Elsevier Science Publishers B.V.
Berge, Stephen M., et al., "Pharmaceutical Salts", Journal of Pharmaceutical Sciences, Jan. 1977, 1-19, vol. 66, No. 1.
Mousa, Shaker A., "Integrins as novel drug discovery targets: potential therapeutic and diagnostic implications", Emerging Therapeutic Targets, 2000, 143-153, Ashley Publications Ltd.
Miller, William H., t al., "Identification and in vivo efficacy of small-molecule antagonists of integrin $\alpha_v\beta_3$ (the vitronectin receptor)", Drug Discovery Today, Sep. 9, 2000, 397-408, vol. 5, No. 9, Elsevier Science Ltd.

(Continued)

Primary Examiner—Deepak Rao
(74) Attorney, Agent, or Firm—Yuriy Strecho

(57) ABSTRACT

The present invention is directed to substituted indanyl compounds of Formula (I):

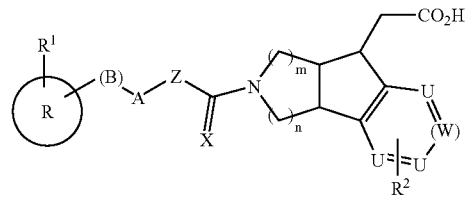

Useful for treating integrin-mediated disorders such as, but not limited to unstable angina, thromboemboic disorders, osteoporosis, growth and metastasis of malignant tumors, diabetic retinopathy, arthritis, viral disease and surgical adhesions.

29 Claims, No Drawings

OTHER PUBLICATIONS

Mousa, Shaker, A., Anti-integrins as a potential therapeutic target in angiogenesis, Expert Opinion on Therapeutic Patents, 1999, 1237-1248, Ashley Publications Ltd.

Hoekstra, William J., et al., "Combinatorial Chemistry Techniques Applied to Nonpeptide Integrin Antagonists", Current Medicinal Chemistry, 1998, 195-204, vol. 5, No. 3, Bentham Science Publishers B.V.

Samanen, James, et al., "Vascular Indications for Integrin $\alpha_v$ Antagonists", Current Pharmaceutical Design, 1997, 545-584, 3, Bentham Science Publishers, B.V.

Varon, David, et al., "Inhibition of Integrin-Mediated Platelet Aggregation, Fibrinogen-Binding, and Interactions with Extracellular Matrix by Nonpeptide Mimetics of Arg-Gly-Asp", Thombosis and Haemostasis, 1993, 1030-1036, 70(6), F.K. Schattauer Verlagsgesellschaft mbH (Stuttgart).

Rodan, S.B., et al., "Integrin function in osteoclasts", Journal of Endocrinology, 1997, S47-S56, 154.

Brooks, Peter C., et al., "Integrin $\alpha_v\beta_3$ Antagonists Promote Tumor Regression by Inducing Apotosis of Angiogenic Blood Vessels", Cell, Dec. 30, 1994, 1157-1164, Cell Press.

Storgard, Chris M., et al., "Decreased angiogenesis and arthritic disease in rabbits treated with an $\alpha_v\beta_3$ antagonist", The Journal of Clinical Investigation, Jan. 1999, 47-54, vol. 103, No. 1.

Friedlander, Martin, et al., "Definition of Two Angiogenic Pathways by Distinct $\alpha_v$ Integrins", Science, Dec. 1995, 1500-1502, vol. 270.

Christofidou-Solomidou, Melpo, et al., "Expression and Function of Endothelial Cell $\alpha_v$ Integrin Receptors in Wound-Induced Human Angiogenesis in Human Skin/SCID Mice Chimeras", American Journal of Pathology, Oct. 1997, 975-983, vol. 151, No. 4, American Society for Investigative Pathology.

Huang, Xiao-Zhu, "Inactivation of the Integrin $\beta_6$ Subunit Gene Reveals a Role of Epithelial Integrins in Regulating Inflammation in the Lungs and Skin", The Journal of Cell Biology, May 1996, 921-928, vol. 133, No. 4, The Rockefeller University Press.

Ross, Russell, "The pathogenesis of atherosclerosis: a perspective for the 1990s", NATURE, Apr. 29, 1993, 801-809, vol. 362.

Cook, C. Edgar, et al., "Structure-Activity Studies of 2,3,4,4a,5,9b-Hexahydroindeno [1,2-c]pyridines as Antispermatogenic Agents for Male Contraception", Journal of Medicinal Chemistry, 1995, 753-763, 38, American Chemical Society.

Clarke, Robert L., et al., "In Pursuit of Analgetic Angets. Hydro-1,3-ethanoindeno[2,1-c]pyridines and Homologs", Journal of Medicinal Chemistry, 1974, 1040-1046, vol. 17, No. 10.

Booth, Raymond G., et al., "Studies on Semirigid Tricyclic Analogues of the Nigrostriatal Toxin 1-Methyl-4-phenyl-1,2,3,6-tetrahydropyridine", Journal of Medicinal Chemistry, 1989, 473-477, vol. 32, No. 2, American Chemical Society.

Achini, Roland, "Synthesis of Phenyl- and Benzyl-Substituted Pyrrolidines and of a Piperidine by Intramolecular C-Alkylation. Synthons for Tricyclic Skeletons", Helvetica Chimica Acta, 1981, 2203-2218, vol. 64 (7), Schweizerische Chemische Gesellschaft.

Nicolaou, K. C., et al., "$HIO_3$ and $I_2O_5$: Mild and Selective Alternative Reagents to IBX for the Dehydrogenation of Aldehydes and Ketones", Angewandte Chemie, Int. Ed., 2002, 1386-1389, vol. 41, No. 8.

Mehta, Raj J., et al., "Transmembrane-truncated $\alpha_v\beta_3$ integrin retains high affinity for ligand binding: evidence for an 'inside-out' suppressor?", Biochem. J., 1998, 861-869, 330.

Hutchinson et al, "Nonpeptide $\alpha_v\beta_3$ Antagonists. 8. In Vitro and In Vivo Evaluation of a Potent $\alpha_v\beta_3$ Antagonist for the Prevention and Treatment of Osteoporosis," J. Med. Chem., 2003, pp. 4790, vol. 46.

Murphy et al "Effect of L-000845704, an $\alpha_v\beta_3$ Integrin Antagonist, on Markers of Bone Turnover and Bone Mineral Density in Postmenopausal Osteoporotic Women,"The Journal of Clinical Endocrinology & Metabolism, 2005, pp. 2022, vol. 90, USA.

Martin et al, "Absence of Adverse Effects in Cynomolgus Macaques Treated with CNTO 95, A Fully Human Anti-$\alpha v$ Integrin Monoclonal Antibody, Despite Widespread Tissue Binding," Clin Cancer Research, 2005, pp. 6959, vol. 11.

Riecke et al, "Topical Application of Integrin Antagonists Inhibits Proliferative Retinopathy," Horm Metab Res., 2001, pp. 307, vol. 33.

Yasukawa et al, "Inhibition of experimental choroidal neovascularization in rats by an $\alpha_v$-integrin antagonist," Current Eye Research, 2004, pp. 359, vol. 28, No. 5.

Miller et al, "Compound 5," J. Med Chem, 2000, pp. 22, vol. 43.

Wilkinson-Berka et al, "SB-267268, A Nonpeptidic Antagonist of $\alpha_v\beta_3$ and $\alpha_v\beta_5$ Integrins, Reduces Angiogenesis and VEGF Expression in a Mouse Model of Retinopathy of Prematurity," Investigative Ophthalmology & Visual Science, 2006, pp. 1600, vol. 47.

Ishida et al, "$VEGF_{164}$-mediated Inflammation Is Required for Pathological, but Not Physiological, Ischemia-induced Retinal Neovascularization," J. Exp. Med., 2003, pp. 483-489, vol. 198.

Moshfeghi et al, "Pegaptanib sodium for the treatment of neovascular age-related macular degeneration," Expert Opinion Investig. Drugs, 2005, pp. 671-682, vol. 14.

* cited by examiner

TRICYCLIC INDANYLS AS INTEGRIN INHIBITORS

This application claims the benefit of Provisional Application 60/491,629 filed Jul. 31, 2003.

FIELD OF THE INVENTION

The present invention is directed to novel compounds, pharmaceutical compositions containing them, and their use as αV integrin inhibitors. More particularly, the tricyclic indanyl derivatives of the present invention are antagonists of the αVβ3, αVβ5 or dual αVβ3/αVβ5 integrin receptors and are useful for treating integrin-mediated disorders such as, but not limited to, unstable angina, thromboemboic disorders, osteoporosis, growth and metastasis of malignant tumors, diabetic retinopathy, arthritis, coronary restenosis, inhibiting viral diseases and surgical adhesions.

BACKGROUND OF THE INVENTION

It is believed that αVβ3 and αVβ5 integrin receptor antagonists can be useful for the treatment of a wide variety of disease states and can represent a new class of drugs. The αVβ3/αVβ5 integrins are cell adhesion receptors which specifically recognize matrix proteins containing the cell-adhesion tripeptide motif arginine-glycine-aspartic acid (RGD). Both integrins are expressed on endothelial cells, smooth muscle cells, osteoclasts and tumor cells, behaving as mediators of cell adhesion, migration, and survival.

Expression of these integrins is typically minimal on normal blood vessels but can be significantly up-regulated in response to a variety of stimuli, leading to such conditions as angiogenesis. Based on results from in vivo animal models, antagonists of αVβ3/αVβ5 integrins may be useful for the treatment of osteoporosis, growth and metastasis of malignant tumors, diabetic retinopathy, arthritis and coronary restenosis (Ref: Miller, W. H., Keenan, R. M.; Willette, R. N.; Lark, M. W., *DDT* 2000, 5 (9), 397-408).

It is an object of the present invention to provide tricyclic indanyl derivatives which are useful αVβ3, αV55 or dual αVβ3/αVβ5 integrin receptor antagonists for the treatment of a wide variety of integrin-mediated disease states. It is another object of the present invention to provide a process for preparing tricyclic indanyl compounds, compositions, intermediates and derivatives thereof.

SUMMARY OF THE INVENTION

The present invention is directed to substituted indanyl compounds of Formula (I):

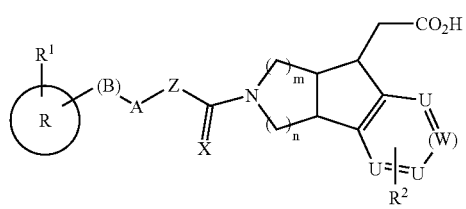

Formula (I)

wherein

R is selected from the group consisting of heterocyclyl and heteroaryl;

$R^1$ is one to two substituents selected from the group consisting of hydrogen, $C_{1-4}$alkyl, $C_{1-4}$alkoxy, hydroxy, —$NR^AR^B$, and halogen;

wherein alkyl and alkoxy are optionally substituted on a terminal carbon one to three substituents independently selected from the group halogen, hydroxy, or —$NR^AR^B$;

wherein $R^A$ and $R^B$ are substituents independently selected from hydrogen or $C_{1-6}$alkyl;

$R^2$ is one to two substituents independently selected from the group consisting of hydrogen, $C_{1-4}$alkyl, $C_{2-6}$alkenyl, $C_{2-6}$alkynyl, $C_{1-4}$alkoxy, —$NR^CR^D$, hydroxy, and halogen;

wherein alkyl, alkenyl, alkynyl, and alkoxy are optionally substituted on a terminal carbon with one to three substituents independently selected from the group halogen, hydroxy, $C_{1-4}$alkoxy, and —$NR^CR^D$;

wherein $R^C$ and $R^D$ are substituents independently selected from hydrogen and $C_{1-6}$-alkyl; $R^C$ and $R^D$ are optionally taken together with the atoms to which they are attached to form a five to seven membered monocyclic ring;

Z is selected from the group consisting of —$CH_2$— and —CH—;

A is selected from the group consisting of aryl, —$CH(CH_2)_{1-3}$—, and —$(CH_2)_{1-3}$—; provided that when A is —$CH(CH_2)_{1-2}$— and Z is —CH— then a double bond is formed between A and Z;

B is —NH— when optionally present;

m and n are integers from 1 to 3;

X is selected from the group consisting of O, S, and two hydrogen atoms;

U is independently selected from —CH—, N, or S, provided that no more than one U represents S or N; and that U can only be S when W is not present;

W is selected from the group consisting of —CH— and N when optionally present;

and enantiomers, diastereomers, tautomers, solvates, or pharmaceutically acceptable salts and medicaments thereof.

The present invention is also directed to methods for producing the instant tricyclic indanyl compounds and pharmaceutical compositions and medicaments thereof.

The present invention is further directed to a method for treating or ameliorating an integrin receptor mediated disorder. These methods of treatments for integrin receptor mediated disorders include but are not limited to unstable angina, thromboemboic disorders, osteoporosis, treating and/or inhibiting restenosis (i.e. recurrence of stenosis after corrective surgery on the heart valve), atherosclerosis, angiogenesis (i.e. formation of new blood vessels), diabetic retinopathy, macular degeneration, growth and metastasis of malignant tumors, arthritis, inhibiting viral disease and surgical adhesions.

Chemical Definitions

As used herein, "halogen" shall mean chlorine, bromine, fluorine and iodine.

As used herein, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein the term "cycloalkyl" refers to an optionally substituted saturated or partially unsaturated monocyclic alkyl ring consisting of 3-8 ring carbon atoms or a saturated or partially unsaturated bicyclic ring consisting of 9 or 10 ring carbon atoms. Examples include, and are not limited to, cyclopropyl, cyclopentyl, cyclohexyl or cycloheptyl.

The term "heterocyclyl" as used herein refers to an unsubstituted or substituted stable three to seven member monocyclic saturated or partially unsaturated ring system which consists of carbon atoms and from one to three heteroatoms selected from N, O or S, or a stable eight to eleven member bicyclic saturated or partially saturated ring system which consists of carbon atoms and from one to four heteroatoms selected from N, O, or S. In either the monocyclic or bicyclic rings the nitrogen or sulfur heteroatoms may optionally be oxidized, and the nitrogen heteroatom may optionally be quaternized. Preferred are saturated or partially unsaturated rings having five or six members of which at least one member is a N, O or S atom and which optionally contains one additional N, O or S atoms; saturated or partially unsaturated bicyclic rings having nine or ten members of which at least one member is a N, O or S atom and which optionally contains one or two additional N, O or S atoms; wherein said nine or ten member bicyclic rings may have one aromatic ring and one nonaromatic ring. The heterocyclyl group may be attached at any heteroatom or carbon atom of the ring such that the result is a stable structure. Preferred examples include, and are not limited to, tetrahydronaphthyridinyl.

The term "aryl" refers to an aromatic monocyclic ring containing carbon and hydrogen, such as a carbon ring containing 6 carbon atom with hydrogen atoms substituted thereon, an aromatic bicyclic ring system containing 10 carbon atoms with hydrogen substituted thereon or an aromatic tricyclic ring system containing 14 carbon atoms with hydrogen atoms substituted thereon. Also included within the scope of the definition of aryl are bicyclic and tricyclic ring systems (containing carbon and hydrogen) wherein only one of the rings is aromatic such as tetrahydronaphthalene and indane. The hydrogen atoms on the monocyclic, bicyclic and tricyclic rings may be replaced with other groups or subsitutents as indicated. Examples include, and are not limited to, phenyl, naphthalenyl or anthracenyl.

The term "heteroaryl" as used herein represents an unsubstituted or substituted stable five or six member monocyclic heteroaromatic ring system or an unsubstituted or substituted stable nine or ten member bicyclic heteroaromatic ring system and unsubstituted or substituted stable twelve to fourteen member tricyclic ring systems which consists of carbon atoms and from one to four heteroatoms selected from N, O or S, and wherein the nitrogen heteroatom of any of these heteroaryls may optionally be oxidized, or may optionally be quaternized. The heteroaryl group may be attached at any heteroatom or carbon atom of the ring such that the result is a stable structure.

The term "arylalkyl" means an alkyl group substituted with an aryl group (e.g., benzyl, phenethyl). The term "arylalkoxy" indicates an alkoxy group substituted with an aryl group (e.g., benzyloxy phenethoxy, etc.). Similarly, the term "aryloxy" indicates an oxy group substituted with an aryl group (e.g., phenoxy).

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

As used herein, the notation "*" shall denote the presence of a stereogenic center.

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

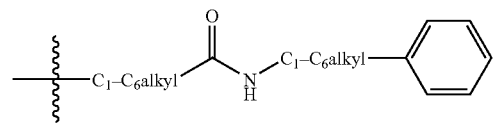

A substituent's point of attachment may also be indicated by a dashed line to indicate the point(s) of attachment, followed by the adjacent functionality and ending with the terminal functionality such as, for example, —($C_{1-6}$)alkyl-C(O)NH—($C_{1-6}$)alkyl-phenyl.

DETAILED DESCRIPTION OF THE INVENTION

Preferred embodiments of the present invention include those compounds of Formula (I):

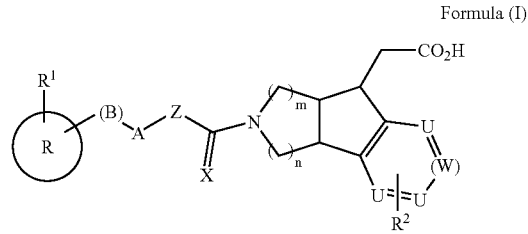

Formula (I)

wherein the compounds is as described herein and R is selected from the group consisting of heterocyclyl and heteroaryl. More preferably, R is 1,4,5,6-tetrahydro-pyrimidin-2-yl, pyridin-2-yl, or 5,6,7,8-tetrahydro-[1,8]naphthyridin-7-yl. Most preferably, R is 1,4,5,6-tetrahydro-pyrimidin-2-yl or 5,6,7,8-tetrahydro-[1,8]naphthyridine-2-yl.

Preferred embodiments of the present invention include those compounds of formula (I) wherein the compound is as described herein and $R^1$ is one to two substituents selected from the group consisting of hydrogen, $C_{1-4}$alkyl, $C_{1-4}$alkoxy, hydroxy, —$NR^AR^B$, and halogen. Preferably, $R^1$ is a substituent selected from the group consisting of hydrogen, $C_{1-4}$alkoxy, —$NR^AR^B$, and hydroxy; wherein $R^A$ and $R^B$ are as previously defined. More preferably, $R^1$ is selected from the group consisting of hydrogen and hydroxy.

Preferred embodiments of the present invention include those compounds of formula (I) wherein the compound is as described herein and $R^2$ is one to two substituents independently selected from the group consisting of hydrogen, $C_{1-4}$alkyl, $C_{1-4}$alkoxy, —$NR^CR^D$, hydroxy, and halogen; wherein alkyl and alkoxy are optionally substituted on a terminal carbon with one to three substituents independently selected from the group halogen, hydroxy, $C_{1-4}$alkoxy, and —$NR^CR^D$; and $R^C$ and $R^D$ are substituents independently selected from hydrogen and $C_{1-6}$-alkyl; $R^C$ and $R^D$ are optionally taken together with the atoms to which they are attached to form a five to seven membered monocyclic ring. More preferably, $R^2$ is a substituent selected from the group consisting of $C_{1-4}$alkoxy, hydrogen, and halogen; wherein alkyl is optionally substituted on a terminal carbon with one to three substituents independently selected from consisting of halogen and hydroxy. Most preferably, $R^2$ is selected from the group consisting of hydrogen, fluorine and $C_{1-4}$alkoxy.

Preferred embodiments of the present invention include those compounds of formula (I) wherein and the compound is as described herein and Z is selected from the group consisting of —$CH_2$— and —CH—. More preferably, Z is —$CH_2$—.

Preferred embodiments of the present invention include those compounds of formula (I) wherein is as described herein and A is selected from the group consisting of aryl, —$CH(CH_2)_{1-2}$—, and —$(CH_2)_{1-3}$—; provided that when A is —$CH(CH_2)_{1-2}$— and Z is —CH— then a double bond is formed between A and Z. More preferably, A is aryl or —$(CH_2)_{1-3}$—; wherein substituents Z and R (or B if present) are attached in meta positions relative to each other.

Preferred embodiments of the present invention include those compounds of formula (I) wherein is as described herein and B is —NH— when optionally present.

Preferred embodiments of the present invention include those compounds of formula (I) wherein is as described herein and m and n are integers from 1 to 3. More preferably, m and n are integers from 1 to 2, provided that m and n are not 2 in the same instance.

Preferred embodiments of the present invention include those compounds of formula (I) wherein is as described herein and X is selected from the group consisting of O and S. More preferably, X is O.

Preferred embodiments of the present invention include those compounds of formula (I) wherein is as described herein and U is independently selected from —CH—, N, and S; provided that no more than one U represents S or N; and that U can only be S when W is not present. More preferably, U is independently selected from —CH— and N; provided that no more than one U represents N.

Preferred embodiments of the present invention include those compounds of formula (I) wherein is as described herein and W is selected from the group consisting of —CH— and N when optionally present.

Preferred embodiments of the present invention include those compounds of formula (I) wherein is as described herein and enantiomers, diastereomers, tautomers, solvates, or pharmaceutically acceptable salts and medicaments thereof.

Embodiments of the present invention include those compounds of Formula (II) shown in Table I. Stereochemistry as defined in Table I describes the relative orientation of the hydrogen substituent at stereocenter 1 to the hydrogen substituent at stereocenters 2 and 3 (centers 2 and 3 are always cis relative to each other). Racemic indicates that that there is a mixture of isomers at stereocenter 1 and the absolute stereochemistry at stereocenters 2 and 3 are not defined.

Formula (II)

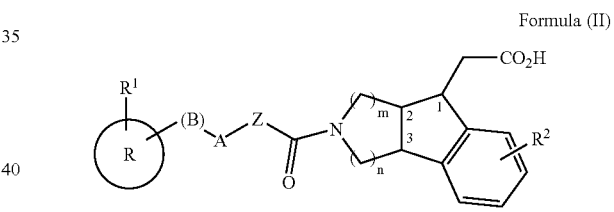

TABLE I

| Cpd | Stereo chem. | R | $R^1$ | B | A | m | n | $R^2$ |
|---|---|---|---|---|---|---|---|---|
| 1 | cis | 1,4,5,6,-tetrahydro-pyrimidin-2-yl | H | NH | 1,3-phenyl | 2 | 1 | H |
| 2 | trans | 1,4,5,6,-tetrahydro-pyrimidin-2-yl | H | NH | 1,3-phenyl | 2 | 1 | H |
| 3 | racemic | 5,6,7,8-tetrahydro-[1,8]naphthyridine-2-yl | H | absent | —$(CH_2)_2$— | 2 | 1 | H |
| 4 | racemic | 5,6,7,8-tetrahydro-[1,8]naphthyridine-2-yl | H | absent | —$(CH_2)$— | 2 | 1 | H |
| 5 | racemic | 1,4,5,6,-tetrahydro-pyrimidin-2-yl | OH | NH | 1,3-phenyl | 2 | 1 | H |
| 6 | cis | Pyridin-2-yl | H | NH | —$(CH_2)_2$— | 2 | 1 | H |
| 7 | trans | Pyridin-2-yl | H | NH | —$(CH_2)_2$— | 2 | 1 | H |
| 8 | racemic | Pyridin-2-yl | H | NH | —$(CH_2)_3$— | 2 | 1 | H |
| 9 | cis | 5,6,7,8-tetrahydro-[1,8]naphthyridine-2-yl | H | absent | —$(CH_2)_2$— | 1 | 2 | H |
| 10 | trans | 5,6,7,8-tetrahydro-[1,8]naphthyridine-2-yl | H | absent | —$(CH_2)_2$— | 1 | 2 | H |
| 11 | racemic | 5,6,7,8-tetrahydro-[1,8]naphthyridine-2-yl | H | absent | —$(CH_2)$— | 1 | 2 | H |
| 12 | racemic | 5,6,7,8-tetrahydro-[1,8]naphthyridine-2-yl | H | absent | —$(CH_2)$— | 1 | 1 | H |

TABLE I-continued

| Cpd | Stereo chem. | R | R¹ | B | A | m | n | R² |
|---|---|---|---|---|---|---|---|---|
| 13* | cis | 5,6,7,8-tetrahydro-[1,8]naphthyridine-2-yl | H | absent | —(CH$_2$)— | 1 | 1 | H |
| 14* | trans | 5,6,7,8-tetrahydro-[1,8]naphthyridine-2-yl | H | absent | —(CH$_2$)— | 1 | 1 | H |
| 15 | racemic | 5,6,7,8-tetrahydro-[1,8]naphthyridine-2-yl | H | absent | —(CH$_2$)$_2$— | 1 | 1 | H |
| 16 | racemic | 5,6,7,8-tetrahydro-[1,8]naphthyridine-2-yl | H | absent | —(CH$_2$)— | 1 | 1 | F |

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1997, Jan, 66(1), p1) include pharmaceutically acceptable acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their pharmaceutically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

Integrins are a widely expressed family of calcium or magnesium dependent α or β heterodimeric cell surface receptors which bind to extracellular matrix adhesive proteins such as fibrinogen, fibronectin, vitronectin and osteopontin. The integrin receptors are transmembrane glycoproteins (GP's) known for their large extracellular domains and are classified by at least 8 known β subunits and 14 α subunits (S. A. Mousa, et al., Emerging Theraupeutic Targets, 2000, 4, (2), 143-153).

For example, the β1 subfamily has the largest number of integrins wherein the various α subunits associate with various β subunits: β3, β5, β6 and β8 (S. A. Mousa, et al., Emerging Theraupeutic Targets, 2000, 4, (2), 144-147). Some of the disease states that have a strong αvβ3, αvβ5 and αIIbβ3 (also referred to as GPIIb/IIIa) integrin component in their etiologies are unstable angina, thromboembolic disorders or atherosclerosis (GPIIb/IIIa); thrombosis or restenosis (GPIIb/IIIa or αvβ3); restenosis (dual αvβ3/GPIIb/IIIa); rheumatoid arthritis, vascular disorders or osteoporosis (αvβ3); tumor angiogenesis, tumor metastasis, tumor growth, multiple sclerosis, neurological disorders, asthma, vascular injury or diabetic retinopathy (αvβ3 or αvβ5); and, angiogenesis (dual αvβ3/αvβ5) (S. A. Mousa, et al., Emerging *Theraupeutic Targets,* 2000, 4, (2), 148-149; W. H. Miller, et al., *Drug Discovery Today* 2000, 5 (9), 397-407; and, S. A. Mousa, et al., *Exp. Opin. Ther. Patents,* 1999, 9 (9), 1237-1248). The β3 subunit has received significant attention in recent drug discovery efforts. (W. J. Hoekstra, *Current Medicinal Chemistry* 1998, 5, 195). Antibodies and/or low-molecular weight compound antagonists of αvβ3 have shown efficacy in animal models (J. Samanen, *Current Pharmaceutical Design* 1997, 3, 545) and, thereby, offer promise as medicinal agents.

Integrin antagonists have typically been designed after the bioactive arginine-glycine-aspartate (RGD) conformation of peptides derived from the primary ligand vitronectin. The RGD motif is the general cell attachment sequence of many extracellular matrix, blood and cell surface proteins, as half of the approximately 20 known integrin bind the RGD-containing adhesion ligands. To discover RGD peptides with integrin selectivity, peptides with both restricted conformations and alterations of flanking residues have been studied. In particular, the structural requirements for interaction of the RGD sequence with GPIIb/IIIa and the inhibitory potential of a series of nonpeptidic mimetics on platelet aggregation and interactions with the extracellular matrix have been described (D. Varon, et al., *Thromb. Haemostasis,* 1993, 70(6), 1030-1036). Iterative synthesis of cyclic and alicyclic peptides and computer modelling have provided potent, selective agents as a platform for nonpeptide αv (as in αvβ3) integrin antagonist design.

Integrin antagonists have been implicated as useful for inhibiting bone resorption (S. B. Rodan and G. A. Rodan, Integrin Function In Osteoclasts, Journal of Endocrinology, 1997, 154: S47-S56). In vertebrates, bone resorption is mediated by the action of cells known as osteoclasts, large multinucleated cells of up to about 400 mm in diameter that resorb mineralized tissue, chiefly calcium carbonate and calcium phosphate. Osteoclasts are actively motile cells that migrate along the surface of bone and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border and secrete lysosomal enzymes and protons to resorb bone. The adhesion of osteoclasts to bone surfaces is an important initial step in bone resorption. In the migratory or motile state, osteoclasts migrate across bone matrix and do not take part in resorption until they again attach to bone.

Integrins are involved in osteoclast attachment, activation and migration. The most abundant integrin receptor on osteoclasts (e.g., on rat, chicken, mouse and human osteoclasts) is the αvβ3 integrin receptor, which is thought to interact in bone with matrix proteins that contain the RGD sequence. Antibodies to αvβ3 block bone resorption in vitro, indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia and glucocorticoid-induced osteoporosis. All of these conditions are characterized by bone loss, resulting from an imbalance between bone resorption, i.e. breakdown and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition that leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two-years, while 30% of the patients require nursing home care after the fracture. Individuals suffering from all the conditions listed above would benefit from treatment with agents that inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration and angiogenesis (i.e. formation of new blood vessels) and inhibiting viral disease.

Moreover, it has been postulated that the growth of tumors depends on an adequate blood supply, which in turn is dependent on the growth of new vessels into the tumor; thus, inhibition of angiogenesis can cause tumor regression in animal models (Harrison's Principles of Internal Medicine, 1991, $12^{th}$ ed.). Therefore, αvβ3 antagonists which inhibit angiogenesis can be useful in the treatment of cancer by inhibiting tumor growth (Brooks et al., *Cell,* 1994, 79, 1157-1164). Evidence has also been presented suggesting that angiogenesis is a central factor in the initiation and persistence of arthritic disease and that the vascular integrin αvβ3 may be a preferred target in inflammatory arthritis. Therefore, αvβ3 antagonists that inhibit angiogenesis may represent a novel therapeutic approach to the treatment of arthritic disease, such as rheumatoid arthritis (C. M. Storgard, et al., Decreased Angiogenesis and Arthritic Disease in Rabbits Treated with an αvβ3 Antagonist, *J. Clin. Invest.,* 1999, 103, 47-54).

Inhibition of the αvβ5 integrin receptor can also prevent neovascularization. A monoclonal antibody for αvβ5 has been shown to inhibit VEGF-induced angiogenesis in rabbit cornea and the chick chorioallantoic membrane model (M. C. Friedlander, et al., *Science,* 1995, 270, 1500-1502). Thus, αvβ5 antagonists are useful for treating and preventing macular degeneration, diabetic retinopathy, cancer and metastatic tumor growth.

Inhibition of αv integrin receptors can also prevent angiogenesis and inflammation by acting as antagonists of other β subunits, such as αvβ6 and αvβ8 (Melpo Christofidou-Solomidou, et al., Expression and Function of Endothelial Cell on Integrin Receptors in Wound-induced Human Angiogenesis in Human Skin/SCID 25 Mice Chimeras, *American Journal of Pathology,* 1997, 151, 975-83; and, Xiao-Zhu Huang, et al., Inactivation of the Integrin β6 Subunit Gene Reveals a Role of Epithelial Integrins in Regulating Inflammation in the Lungs and Skin, *Journal of Cell Biology,* 1996, 133, 921-28).

An aspect of the invention is a composition or medicament comprising a pharmaceutically appropriate carrier and any of the compounds of the present invention. Illustrative of the invention is a composition or medicament made by mixing an instant compound and a pharmaceutically appropriate carrier. Another illustration of the invention is a process for making a composition or medicament comprising mixing any of the compounds described above and a pharmaceutically appropriate carrier. Further illustrative of the present invention are compositions or medicaments comprising one or more compounds of this invention in association with a pharmaceutically appropriate carrier.

As used herein, the term "composition" is intended to encompass a product comprising the specified ingredients in the specified amounts, as well as any product which results, directly or indirectly, from combinations of the specified ingredients in the specified amounts for treating or ameliorating an αv integrin mediated disorder or for use as a medicament.

The compounds of the present invention are αv integrin inhibitors useful for treating or ameliorating an αv integrin mediated disorder. An aspect of the invention includes compounds that are selective inhibitors of an αv integrin receptor, or subtype thereof. In another aspect of the invention, the inhibitor is independently selective to the αvβ3 integrin receptor or the αvβ5 integrin receptor. An aspect of the invention also includes compounds that are inhibitors of a combination of αv integrin receptors, or subtypes thereof. In another aspect of the invention, the compound inhibitor simultaneously antagonizes both the αvβ3 integrin and the αvβ5 integrin receptor subtypes.

An aspect of the present invention includes a method for treating or ameliorating an αv integrin mediated disorder in a subject in need thereof comprising administering to the subject a therapeutically effective amount of a compound of Formula (I) or composition thereof.

The term "therapeutically effective amount" or "effective amount," as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

An aspect of the present invention includes a prophylactic method for preventing an αv integrin mediated disorder in a subject in need thereof comprising administering to the subject a prophylactically effective amount of a compound of Formula (I) or composition thereof.

Another aspect of the present invention includes the preparation of a medicament comprising a therapeutically effective amount of a compound of Formula (I) for use in preventing, treating or ameliorating an αv integrin mediated disorder in a subject in need thereof.

The term "administering" is to be interpreted in accordance with the methods of the present invention whereby an individual compound of the present invention or a composition thereof can be therapeutically administered separately at different times during the course of therapy or concurrently in divided or single combination forms. Prophylactic administration can occur prior to the manifestation of symptoms characteristic of an αv integrin mediated disease or disorder such that the disease or disorder is prevented or, alternatively, delayed in its progression. The instant invention is therefore to be understood as embracing all such regimes of simultaneous or alternating therapeutic or prophylatic treatment.

The term "subject" as used herein, refers to an animal, preferably a mammal, most preferably a human, which has been the object of treatment, observation or experiment and is at risk of (or susceptible to) developing a disease or disorder or having a disease or disorder related to expression of an αv integrin, or subtype thereof.

The term "αv integrin mediated disorder" refers to disorders and diseases associated with pathological unregulated or disregulated cell proliferation resulting from expression of an αv integrin, or subtype thereof.

The term "unregulated" refers to a breakdown in the process of regulating cell proliferation, as in a tumor cell. The term "disregulated" refers to inappropriate cell growth as a result of pathogenesis. The term "subtype" refers to a particular αv integrin receptor selected from those receptors making up the class of αv integrins, such as an αvβ3 integrin receptor or an αvβ5 integrin receptor.

The term "disorders and diseases associated with unregulated or disregulated cell proliferation" refers to disorders wherein cell proliferation by one or more subset of cells in a multicellular organism results in harm (such as discomfort or decreased life expectancy) to the organism. Such disorders can occur in different types of animals and humans and include, and are not limited to, cancers, cancer-associated pathologies, atherosclerosis, transplantation-induced vasculopathies, neointima formation, papilloma, lung fibrosis, pulmonary fibrosis, glomerulonephritis, glomerulosclerosis, congenital multicystic renal dysplasia, kidney fibrosis, diabetic retinopathy, macular degeneration, psoriasis, osteoporosis, bone resorption, inflammatory arthritis, rheumatoid arthritis or restenosis.

The term "cancers" refers to, and is not limited to, glioma cancers, lung cancers, breast cancers, colorectal cancers, prostate cancers, gastric cancers, esophageal cancers, leukemias, melanomas, basal cell carcinomas and lymphomas. The term "cancer-associated pathologies" refers to, and is not limited to, unregulated or disregulated cell proliferation, tumor growth, tumor vascularization, angiopathy and angiogenesis. The term "angiogenesis" refers to, and is not limited to, unregulated or disregulated proliferation of new vascular tissue including, but not limited to, endothelial cells, vascular smooth muscle cells, pericytes and fibroblasts. The term "osteoporosis" refers to, and is not limited to, formation or activity of osteoclasts resulting in bone resorption. The term "restenosis" refers to, and is not limited to, in-stent stenosis and vascular graft restenosis.

The term "αv integrin expression" refers to expression of an αv integrin, or subtype thereof, which leads to unregulated or disregulated cell proliferation:
1. by cells which do not normally express an αv integrin, or subtype thereof,
2. by neoplastic cells,
3. in response to stimulation by a growth factor, hypoxia, neoplasia or a disease process,
4. as a result of mutations which lead to constitutive expression of an αv integrin, or subtype thereof.

The expression of an αv integrin, or subtype thereof, includes selective expression of an αv integrin or subtype thereof, selective expression of the αvβ3 integrin or the αvβ5 integrin subtypes, expression of multiple αv integrin subtypes or simultaneous expression of the αvβ3 integrin and the αvβ5 integrin subtypes. Detecting the expression of an αv integrin, or subtype thereof, in inappropriate or abnormal levels is determined by procedures well known in the art.

Another aspect of the present invention includes a method for treating or ameliorating a selective αvβ3 integrin mediated disorder in a subject in need thereof comprising administering to the subject a therapeutically effective amount of a compound of Formula (I) or composition thereof.

Another aspect of the present invention includes a method for treating or ameliorating a selective αvβ5 integrin mediated disorder in a subject in need thereof comprising administering to the subject a therapeutically effective amount of a compound of Formula (I) or composition thereof.

Another aspect of the present invention includes a method for treating or ameliorating a disorder simultaneously mediated by an αvβ3 and αvβ5 integrin in a subject in need thereof comprising administering to the subject a therapeutically effective amount of a compound of Formula (I) or composition thereof.

An aspect of the present invention includes a method for inhibiting αv integrin mediated neoplastic activity comprising administering to a neoplasm or to the microenvironment around the neoplasm an effective amount of a compound of Formula (I) or composition thereof.

The term "neoplastic activity" refers to unregulated or disregulated cell proliferation and the process of angiogenesis or the formation of new vasculature supporting a neoplasm in the endothelial microenvironment around the neoplasm.

The term "neoplasm" refers to tumor cells are cells having unregulated or disregulated proliferation as a result of genetic instability or mutation and an endothelium wherein the endothelial cells have unregulated or disregulated proliferation as a result of a pathogenic condition. Within the scope of the present invention, a neoplasm is not required to express the αv integrin, or subtype thereof, by itself and is not limited to a primary tumor of origin but also to secondary tumors occurring as a result of metastasis of the primary tumor. The term "administering to a neoplasm" refers to administering a compound of Formula (I) or composition thereof to the surface of a neoplasm, to the surface of a neoplastic cell or to the endothelial microenvironment around a neoplasm.

The term "inhibiting αv integrin mediated neoplastic activity" includes attenuating a tumor's growth by limiting its blood supply and, further, preventing the formation of new supportive vasculature by preventing the process of angiogenesis.

An aspect of the present invention includes a method for treating or ameliorating a disease mediated by cells pathologically expressing an αv integrin, or subtype thereof.

The term "disease mediated by cells pathologically expressing an αv integrin" refers to, and is not limited to, a disorders selected from cancers, cancer-associated pathologies, diabetic retinopathy, macular degeneration, osteoporosis, bone resorption, inflammatory arthritis, rheumatoid arthritis or restenosis.

An aspect of the present invention includes a method for use of a compound of Formula (I) or composition thereof advantageously co administered in one or more tumor or cell anti-proliferation therapies including chemotherapy, radiation therapy, gene therapy or immunotherapy for preventing, treating or ameliorating an αv integrin mediated disorder.

The combination therapy can include:
1. co-administration of a compound of Formula (I) or composition thereof and a chemotherapeutic agent for preventing, treating or ameliorating an αv integrin mediated disorder,
2. sequential administration of a compound of Formula (I) or composition thereof and a chemotherapeutic agent for preventing, treating or ameliorating an αv integrin mediated disorder,
3. administration of a composition containing a compound of Formula (I) and a chemotherapeutic agent for preventing, treating or ameliorating an αv integrin mediated disorder, or,
4. simultaneous administration of a separate composition containing a compound of Formula (I) and a separate composition containing a chemotherapeutic agent for preventing, treating or ameliorating an αv integrin mediated disorder.

For example, the compounds of this invention are useful in combination therapies with at least one other chemotherapeutic agent for the treatment of a number of different cancers and advantageously appear to facilitate the use of a reduced dose of the chemotherapeutic agent that is recommended for a particular cancer or cell proliferation disorder. Therefore, it is contemplated that the compounds of this invention can be used in a treatment regime before the administration of a particular chemotherapeutic agent recommended for the treatment of a particular cancer, during administration of the chemotherapeutic agent or after treatment with a particular chemotherapeutic agent.

The term "chemotherapeutic agents" includes, and is not limited to, anti-angiogenic agents, anti-tumor agents, cytotoxic agents, inhibitors of cell proliferation and the like. The term "treating or ameliorating" includes, and is not limited to, facilitating the eradication of, inhibiting the progression of or promoting stasis of a malignancy. For example, an inhibitor compound of the present invention, acting as an anti-angiogenic agent can be administered in a dosing regimen with at least one other cytotoxic compound, such as a DNA alkylating agent.

Preferred anti-tumor agents are selected from the group consisting of cladribine (2-chloro-2'-deoxy-(beta)-D-adenosine), chlorambucil (4-(bis(2-chloroethyl)amino)benzenebutanoic acid), DTIC-Dome (5-(3,3-dimethyl-1-triazeno)-imidazole-4-carboxamide), platinum chemotherapeutics and nonplatinum chemotherapeutics. Platinum containing anti-tumor agents include, and are not limited to, cisplatin (CDDP) (cis-dichlorodiamineplatinum). Non-platinum containing anti-tumor agents include, and are not limited to, adriamycin (doxorubicin), aminopterin, bleomycin, camptothecin, carminomycin, combretastatin(s), cyclophosphamide, cytosine arabinoside, dactinomycin, daunomycin, epirubicin, etoposide (VP-16), 5-fluorouracil (5FU), herceptin actinomycin-D, methotrexate, mitomycin C, tamoxifen, taxol, taxotere, thiotepa, vinblastine, vincristine, vinorelbine and derivatives and prodrugs thereof. Each anti-tumor agent is administered in a therapeutically effective amount, which varies based on the agent used, the type of malignancy to be treated or ameliorated and other conditions according to methods well known in the art.

As will be understood by those skilled in the art, the appropriate doses of chemotherapeutic agents will be generally around those already employed in clinical therapies wherein the chemotherapeutics are administered alone or in combination with other chemotherapeutics. By way of example only, agents such as cisplatin and other DNA alkylating are used widely to treat cancer. The efficacious dose of cisplatin used in clinical applications is about 20 mg/m$^2$ for 5 days every three weeks for a total of three courses. Cisplatin is not absorbed orally and must therefore be delivered via injection intravenously, subcutaneously, intratumorally or intraperitoneally. Further useful agents include compounds that interfere with DNA replication, mitosis and chromosomal segregation. Such chemotherapeutic agents include adriamycin (doxorubicin), etoposide, verapamil or podophyllotoxin and the like and are widely used in clinical settings for tumor treatment. These compounds are administered through bolus injections intravenously at doses ranging from about 25 to about 75 mg/m$^2$ at 21 day intervals (for adriamycin) or from about 35 to about 50 mg/m$^2$ (for etoposide) intravenously or at double the intravenous dose orally. Agents that disrupt the synthesis and fidelity of polynucleotide precursors such as 5-fluorouracil (5-FU) are preferentially used to target tumors. Although quite toxic, 5-FU is commonly used via intravenous administration with doses ranging from about 3 to about 15 mg/kg/day.

Another aspect of the present invention includes a method for administering a compound of the present invention in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

Coronary angioplasty is a highly effective procedure used to reduce the severity of coronary occlusion; however, its long-term success is limited by a high rate of restenosis. Vascular smooth muscle cell activation, migration and proliferation is largely responsible for restenosis following angioplasty (Ross, R., Nature, 1993, 362, 801-809).

An aspect of the present invention includes a method for use of αv integrin inhibitor compound of Formula (I) or composition thereof for treating or ameliorating arterial and venous restenosis; wherein the compound is impregnated on the surface of a therapeutic device. The term "therapeutic device" refers to, and is not limited to, an angioplasty balloon, arterial stent, venous stent, suture, artificial joint, implanted prosthesis or other like medical devices, thus targeting drug delivery to a neoplasm.

An aspect of the present invention includes a method for use of αv integrin inhibitor compound of Formula (I) or composition thereof for treating or ameliorating of postoperative adhesions associated with surgical procedures. In this embodiment of the invention a patient would receive at therapeutic dosage either preoperatively, during surgery or postoperatively would be administered the compounds of Formula (I) to ameliorate the formation of adhesions for example associated with abdominal surgery.

An aspect of the present invention includes a composition comprising a compound of Formula (I), or pharmaceutically acceptable salt thereof, in association with a pharmaceutically acceptable carrier. Compositions contemplated within this invention can be prepared according to conventional pharmaceutical techniques. A pharmaceutically acceptable carrier may also (but need not necessarily) be used in the composition of the invention.

The term "pharmaceutically acceptable" refers to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

The composition may take a wide variety of forms depending on the form of preparation desired for administration including, but not limited to, intravenous (both bolus and infusion), oral, nasal, transdermal, topical with or without occlusion, and injection intraperitoneally, subcutaneously, intramuscularly, intratumorally or parenterally, all using forms well known to those of ordinary skill in the pharmaceutical arts. The composition may comprise a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition may be presented in a form suitable for once-weekly or once-monthly administration; for example, an insoluble salt of the active compound, such as the decanoate salt, may be adapted to provide a depot preparation for intramuscular injection. In preparing the compositions in oral dosage form, one or more of the usual pharmaceutical carriers may be employed, including necessary and inert pharmaceutical excipients, such as water, glycols, oils, alcohols, flavoring agents, preservatives, coloring agents, syrup and the like; in the case of oral liquid preparations, carriers such as starches, sugars, diluents, granulating agents, lubricants, binders, disintegrating agents and the like may be employed.

The dosage unit (tablet, capsule, powder, injection, suppository, measured liquid dosage and the like) containing the pharmaceutical compositions herein will contain an amount of the active ingredient necessary to deliver a therapeutically effective amount as described above. The composition may contain from about 0.001 mg to about 5000 mg of the active compound or prodrug thereof and may be constituted into any form suitable for the mode of administration selected for a subject in need.

An aspect of the present invention contemplates a therapeutically effective amount in a range of from about 0.001 mg to 1000 mg/kg of body weight per day. Another aspect of the present invention includes a range of from about 0.001 to about 500 mg/kg of body weight per day. A further aspect of the present invention includes a range of from about 0.001 to about 300 mg/kg of body weight per day. The compounds may be administered according to a dosage regimen of from about 1 to about 5 times per day and still more preferably 1, 2 or 3 times a day.

For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages to be administered may be readily determined by those skilled in the art and will vary depending on factors associated with the particular patient being treated (age, weight, diet and time of administration), the severity of the condition being treated, the compound being employed, the mode of administration and the strength of the preparation. The use of either daily administration or post-periodic dosing may be employed.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.001 to about 5000 mg of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

For oral administration in the form of a tablet or capsule, the active drug component can be optionally combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the compound of formula (I) may be incorporated for administration orally or by injection include, aqueous solutions, suitably flavored syrups, aqueous or oil suspensions and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations that generally contain suitable preservatives are employed when intravenous administration is desired.

As is also known in the art, the compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cottonseed oil, sesame oil and the like, as well as organic solvents such as solketal, glycerol and the like. As an alternative, aqueous parenteral formulations may also be used. For example, acceptable aqueous solvents include water, Ringer's solution and an isotonic aqueous saline solution. Further, a sterile non-volatile oil can usually be employed as a solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

Advantageously, compounds of Formula (I) may be administered in a single daily dose, or the total daily dosage may be administered in divided doses of two, three or four times daily. Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Because of their ease of administration, tablets and capsules represent an advantageous oral dosage unit form, wherein solid pharmaceutical carriers are employed. If desired, tablets may be sugarcoated or enteric-coated by standard techniques. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The compositions of the present invention also include a composition for slow release of the compound of the invention. The composition includes a slow release carrier (typically, a polymeric carrier) and a compound of the invention. In preparation for slow release, a slow release carrier, typically a polymeric carrier and a compound of the invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the invention. Slow release biodegradable carriers are also well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter and most preferably about 100 nm in diameter).

The present invention also provides methods to prepare the pharmaceutical compositions of this invention. A compound of Formula (I) as the active ingredient is intimately admixed with a pharmaceutical carrier according to conventional pharmaceutical compounding techniques, which carrier may take a wide variety of forms depending on the form of preparation desired for administration. In preparing the compositions in oral dosage form, any of the usual pharmaceutical media may be employed. For solid oral dosage forms, suitable carriers and additives include starches, sugars, diluents, granulating agents, lubricants, binders, disintegrating agents and the like. For liquid oral preparations, suitable carriers and additives include water, glycols, oils, alcohols, flavoring agents, preservatives, coloring agents and the like. Additionally, liquid forms of the active drug component can be combined in suitably flavored suspending or dispersing agents such as the synthetic and natural gums, including for example, tragacanth, acacia, methyl-cellulose and the like. Other dispersing agents that may be employed include glycerin and the like.

Although any linking moiety that is reasonably stable in blood can be used to link the compound of the invention to the targeting agent, those with biologically-releasable bonds and/or selectively cleavable spacers or linkers are preferred. "Biologically-releasable bonds" and "selectively cleavable spacers or linkers" refers to those linking moieties which have reasonable stability in the circulation and are releasable, cleavable or hydrolyzable only or preferentially under certain conditions, (i.e., within a certain environment or in contact with a particular agent). Such bonds include, for example, disulfide and trisulfide bonds and acid-labile bonds (as described in U.S. Pat. Nos. 5,474,765 and 5,762,918) and enzyme-sensitive bonds, including peptide bonds, esters, amides, phosphodiesters and glycosides (as described in U.S. Pat. Nos. 5,474,765 and 5,762,918). Such selective-release design features facilitate sustained release of the compounds from the conjugates at the intended target site.

The therapeutically effective amount of a compound of the invention conjugated to a targeting agent depends on the individual, the disease type, the disease state, the method of administration and other clinical variables. The effective amount is readily determinable using data from an animal model. Experimental animals bearing solid tumors are frequently used to optimize appropriate therapeutically effective amounts prior to translating to a clinical environment. Such models are known to be very reliable in predicting effective anti-cancer strategies. For example, mice bearing solid tumors are widely used in pre-clinical testing to determine working ranges of therapeutic agents that give beneficial anti-tumor effects with minimal toxicity.

The present invention further provides a composition that comprises an effective amount of the compound of the invention conjugated to a targeting agent and a pharmaceutically acceptable carrier. When proteins such as antibodies or growth factors, or polysaccharides are used as targeting agents, they are preferably administered in the form of injectable compositions. The injectable antibody solution will be administered into a vein, artery or into the spinal fluid over the course of from about 2 minutes to about 45 minutes, preferably from about 10 to about 20 minutes. In certain cases, intradermal and intracavitary administration are advantageous for tumors restricted to areas close to particular regions of the skin and/or to particular body cavities. In addition, intrathecal administrations may be used for tumors located in the brain.

Another aspect of the present invention includes a method for treating or disorders related to $\alpha v$ integrin expression (in particular, restenosis, intimal hyperplasia or inflammation in vessel walls) in a subject in need thereof comprising administering to the subject by controlled delivery a therapeutically effective amount of a compound of Formula (I) or composition thereof coated onto an intraluminal medical device (in particular, a balloon-catheter or stent). Such devices are useful to prevent the occurrence of restenosis by inhibiting $\alpha v$ integrin activity and thus preventing hyperproliferation of the endothelium.

The term "intraluminal medical device" refers to any delivery device, such as intravascular drug delivery catheters, wires, pharmacological stents and endoluminal paving. The scope of the present invention includes delivery devices comprising an arterial or venous stent having a coating or sheath which elutes or releases a therapeutically effective amount of an instant compound. The term "controlled delivery" refers to the release of active ingredient in a site-directed and time dependent manner. Alternatively, the delivery system for such a device may comprise a local infusion catheter that delivers the compound at a variably controlled rate.

The term "stent" refers to any device capable of being delivered by a catheter. A stent is routinely used to prevent vascular closure due to physical anomalies such as unwanted inward growth of vascular tissue due to surgical trauma. A stent often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent material may be a polymeric, metallic or a combination polymeric-metallic material and can be optionally biodegradable.

Commonly, a stent is inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in pending U.S. Patent application 2002/0016625 A1 (Falotico, et al.) may also be utilized. The combination of a stent with drugs, agents or compounds which prevent inflammation and proliferation may provide the most efficacious treatment for post-angioplasty restenosis.

Compounds of the present invention can be incorporated into or affixed to the stent in a number of ways. A solution of the compound of the invention and a biocompatible material or polymer may be incorporated into or onto a stent in a number of ways. For example, a solution of an instant compound may be sprayed onto the stent or the stent may be dipped into the solution and, in each case, allowed to dry. Another coating method electrically charges a solution of an instant compound to one polarity and charges the stent to the opposite polarity. In this manner, the solution and stent will be attracted to one another. Another method coats the stent with a solution of an instant compound using supercritical temperature and pressure conditions. Coating the stent using supercritical conditions reduces waste and allows more control over the thickness of the coat may be achieved. The compound is usually only affixed to the outer surface of the stent (the surface which makes contact with the tissue), but for some compounds, the entire stent may be coated.

A combination product comprising a therapeutically effective amount of an instant compound coated on the stent and on or in a layer or layers of a polymer coating wherein the polymer coating controls the release rate of the drug may be used when the effectiveness of the drug is affected. Accordingly, the compound may be released from the stent over a period of at least about 6 months; in another aspect, over a period of about 3 days to about 6 months; and, in another aspect over a period of about 7 to about 30 days. Any number of non-erodible, biocompatible polymeric materials may be used for the polymer coating layer or layers in conjunction with the compound of the invention.

In one illustration, the compound is directly incorporated into a polymeric matrix, such as the polymer polypyrrole and subsequently coated onto the outer surface of the stent. Essentially, the compound elutes from the matrix by diffusion through the polymer molecules. Stents and methods for coating drugs on stents are discussed in detail in PCT application WO 96/32907. In another aspect, the stent is first coated with as a base layer comprising a solution of the compound, ethylene-co-vinylacetate and polybutylmethacrylate. The stent is then further coated with an outer layer comprising polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in pending U.S. Patent application 2002/0016625 A1.

It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium or shape-retentive polymeric materials that "remember" and return to their original shape upon activation at body temperature.

Methods for introducing a stent into a lumen of a body are well known. In an aspect of this invention, a compound-coated stent is introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells or by changes in the vascular resistance or lumen diameter. Optimum conditions can be determined based on data from animal model studies using routine computational methods.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

Abbreviations used in the specification, particularly the Schemes and Examples, are as follows:

| | |
|---|---|
| ACE-Cl = | 1-Chloroethyl chloroformate |
| Ar = | Aryl group |
| AcOH = | Acetic acid |
| DCC = | 1,3-Dicyclohexylcarbodiimide |
| DEA = | diethylamine |
| DEAD = | Diethylazodicarboxylate |
| DIAD = | Diisopropylazodicarboxylate |
| DIPEA or DIEA = | Diisopropylethylamine |
| DMAP = | 4-N,N-Dimethylaminopyridine |
| DMF = | N,N-Dimethylformamide |
| DMSO = | Dimethylsulfoxide |
| $D_2O$ = | Deuterated water |
| $Et_3N$ = | Triethylamine |
| $Et_2O$ = | Diethyl ether |
| EtOAc = | Ethyl acetate |
| EtOH = | Ethanol |

-continued

| | |
|---|---|
| HATU = | O-(7-Azabenzotriazol-1-yl)-N,N,N'',N''-Tetramethyl Uronium Hexafluorophosphate |
| HEPES = | 4-(2-Hydroxyethyl)-1-Piperizine Ethane Sulfonic Acid |
| HOBT = | 1-Hydroxybenzotriazole |
| HPLC = | High Pressure Liquid Chromatography |
| HBTU = | o-Benzotriazol-1-yl-N,N,N',N'-tetramethyluronium hexafluorophosphate |
| LiOH = | Lithium Hydroxide |
| MeOH = | Methanol |
| NaHMDS = | Sodium hexamethyldisilazane |
| NaOEt = | Sodium Ethoxide |
| NMM = | N-methylmorpholine |
| NT = | Not tested |
| PBS = | Phosphate Buffered Saline |
| Pd-C = | Palladium on Carbon Catalyst |
| $Pd_2(OAc)_2$ = | Palladium(II)acetate |
| Ph = | Phenyl |
| PPA = | Polyphosphoric acid |
| $PtO_2$ = | Platinum (IV) oxide |
| RT or rt = | Room temperature |
| t-BOC or Boc = | Tert-Butoxycarbonyl |
| TEA = | Triethylamine |
| TFA = | Trifluoroacetic Acid |
| THF = | Tetrahydrofuran |
| TLC = | Thin Layer Chromatography |
| TMOF = | Trimethylorthoformate |
| Tris HCl or Tris-Cl = | Tris[hydroxymethyl]aminomethyl hydrochloride |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds of the present invention and stereoisomers, racemic mixtures, diastereomers and enantiomers thereof can be synthesized using the intermediates prepared in accordance with Scheme AA and Scheme BB, and other materials, compounds and reagents known to those skilled in the art. All such compounds, stereoisomers, racemic mixtures, diastereomers and enantiomers thereof are intended to be encompassed within the scope of the present invention. Since the schemes are an illustration, the invention should not be construed as being limited by the chemical reaction and conditions expressed. The preparation of the various starting materials used in the scheme is well within the skill of persons versed in the art.

Scheme AA describes a general method for preparing compounds of the invention. The 6-5-6 tricyclic ring system of Compound AA3 wherein x is 2 and y is 1 was constructed in three steps according to a literature method (Paragamian, Vasken; U.S. Pat. No. 3,462,443, Aug. 19, 1969 and Cook, C. E.; Wani, M. C.; Jump, J. M.; Lee, Y-W; Fail, P. A.; Anderson, S. A.; Gu, Y-Q.; Petrow, V.; J. Med. Chem. 1995, 38, 753-763). Other compounds of the present invention having a 6-5-6 tricycle wherein x is 1 and y is 2 were prepared using appropriate reagents and starting materials known to those skilled in the art according to the literature method (Clark, R. L.; Gambino, A. J.; Daum, S. J.; J. Med. Chem 1974, 17 (10), 1040-1046; Booth, R. G; Trevor, A; Singer, T. P. Castagnoli, N; J. Med. Chem. 1989, 32 (2), 473-477). The 6-5-6 tricyclic ring systems described supra were reacted similarly to prepare the compounds of the present invention as described below.

Compound AA3 was treated with a Horner-Emmon's reagent, trimethylphosphonoacetate Compound AA4, to furnish Compound AA5 as a mixture of E,Z-isomers. Compound AA5 was reduced by hydrogenation to yield one predominant isomer Compound AA6, assumed to be the all cis-hydrogen ring system. Compound AA6 was N-demethylated by treatment with ACE-Cl to yield Compound AA7. Compounds of the present invention were prepared by attaching a variety of carboxylic acids, Compound AA8, to the amine of Compound AA7 using an appropriate coupling agent, base, activating agent, and solvent to provide Compound AA9. An appropriate coupling agent may include, and is not limited to HTBU, DCC, and the like; an appropriate base may include, and is not limited to NMM; an appropriate activating agent may include, but is not limited to, HOBt; and an appropriate solvent may include, but is not limited to, DMF or $CH_2Cl_2$. For compounds of the present invention, Compound AA7 was acylated in the presence of HOBt, HTBU, NMM and DMF.

Compound AA9 was saponified with lithium hydroxide to give the free acids AA10 and AA11 as a mixture of diasteromers. These isomers were separated by HPLC when achievable.

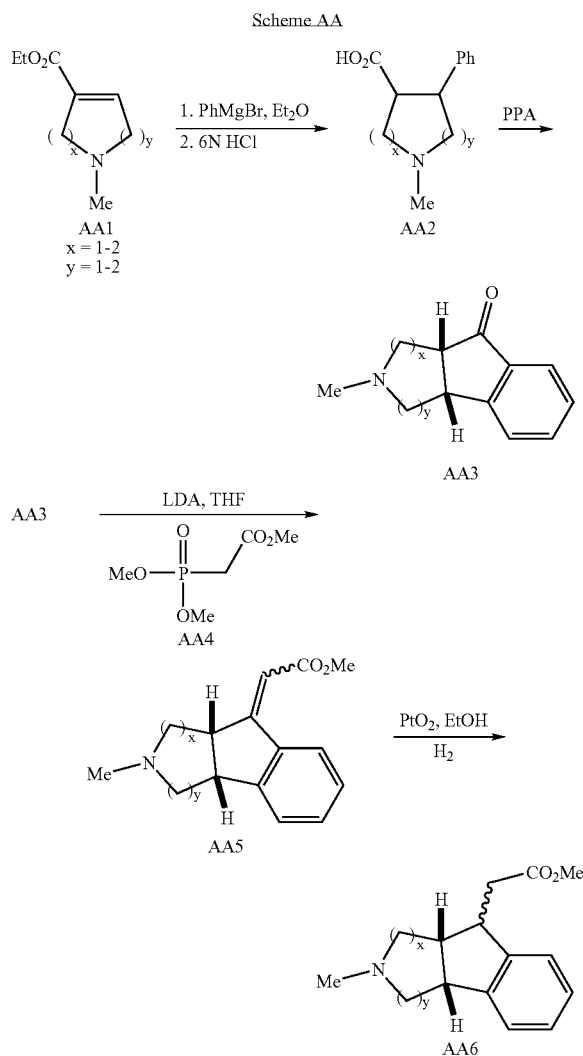

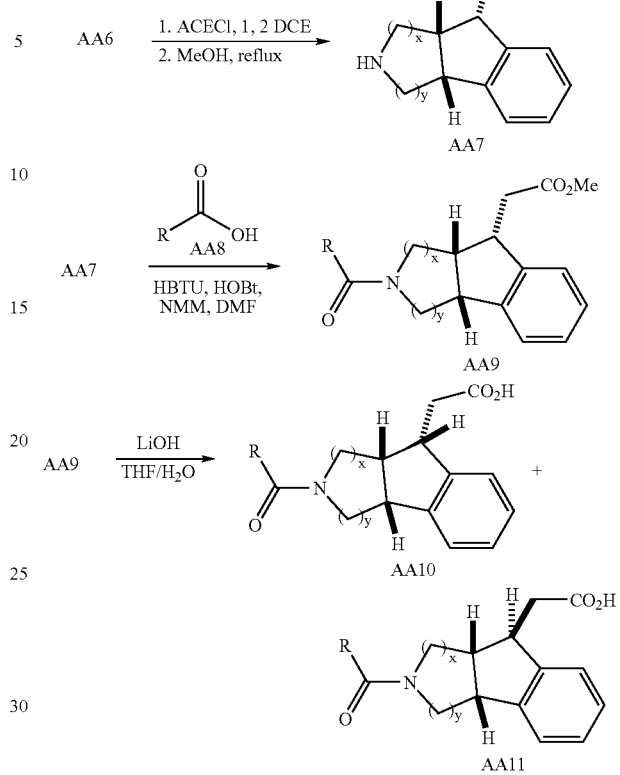

Scheme BB describes a general method for the preparation of compounds of the present invention that contain a 5-5-6 tricyclic ring system. While a literature method for making such a ring system was available, (*Helvetica Chemica Acta* 1981, 64, (7), 2203-2218), a more convenient and novel route was used in the present invention, as illustrated in Scheme BB.

Compound BB1 was reacted with TFA to form an ylide that underwent a 1,3-dipolar cycloaddition with trans-cinnamic acid methyl ester to afford Compound BB2. Compound BB2 was hydrolyzed under basic conditions to carboxylic acid BB3. Compound BB3 was treated with PPA to provide cyclized product Compound BB4. Compound BB4 was also prepared by the reaction of the ylide derived from Compound BB1 with indenone. Compound BB4 was initially taken through the synthetic sequence as a mixture of enantiomers, but Compound BB4 was also separated into its two enantiomers, Compounds BB5 and BB6. For example, Compound BB5 (assumed to be predominantly the cis enantiomer) was treated with the Horner-Emmon's reagent, trimethylphosphonoacetate Compound AA4 to furnish Compound BB7 as a mixture of E,Z-isomers. Compound BB7 was reduced by hydrogenation at elevated temperatures to yield amine Compounds BB8 as a mixture of isomers in an approximate 1:1 ratio. Compounds of the present invention were prepared by attaching a variety of carboxylic acids Compound AA8 to the amine of Compound BB8 using an appropriate coupling agent, base, activating agent, and solvent to provide Compound BB9. An appropriate coupling agent may include, and is not limited to HTBU, DCC, and the like; an appropriate base may include, and is not limited to NMM; an appropriate activating agent may include, but is not limited to, HOBt; and an appropriate solvent may include, but is not limited to, DMF or $CH_2Cl_2$. For compounds of the present invention, Compound BB8 was acylated in the presence of HOBt, HTBU, NMM and DMF. Compound BB9 was saponified with lithium hydroxide to give the free acids BB10 and BB11 as a mixture of diasteromers, which were separated by HPLC.

EXAMPLES

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

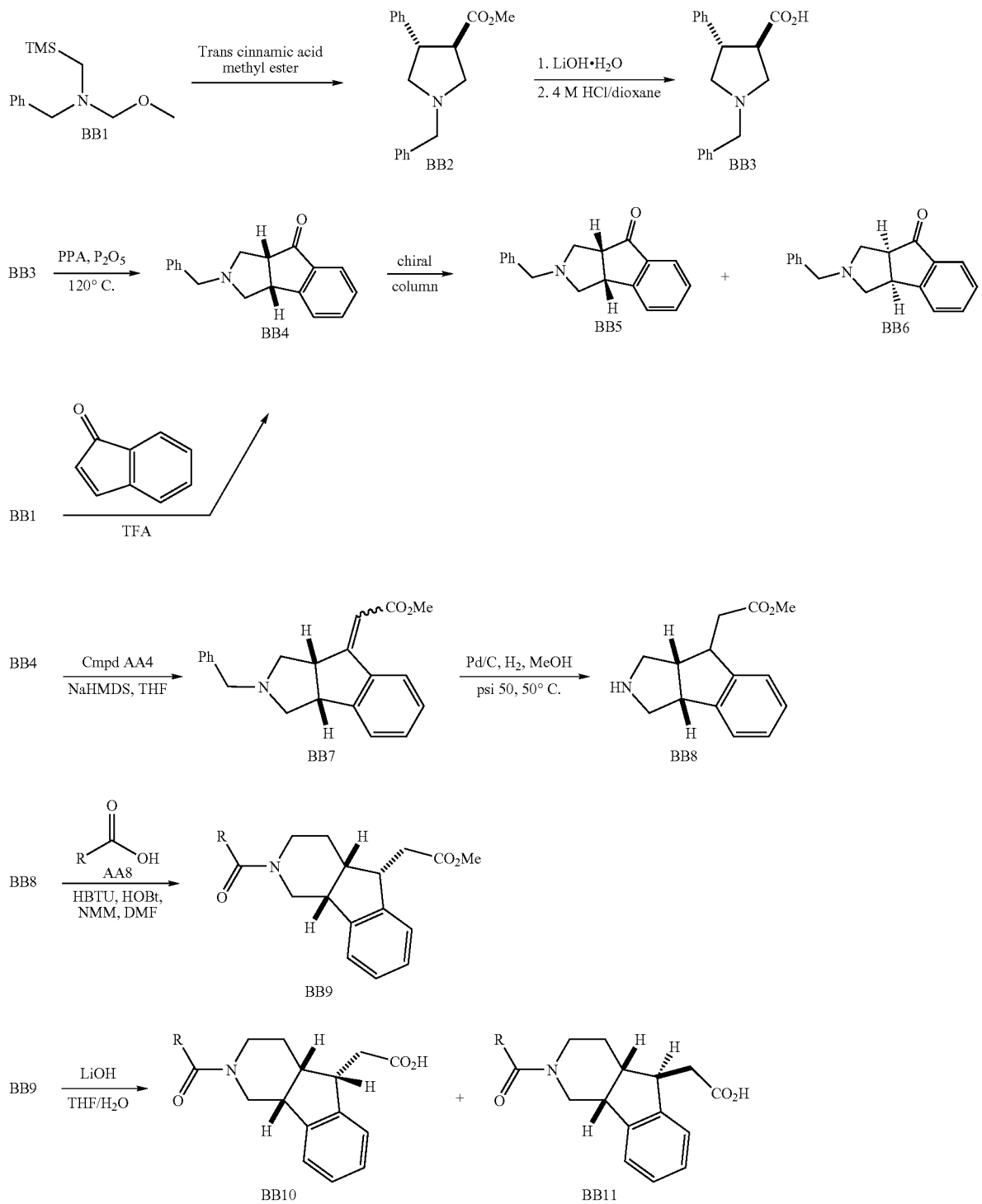

Example 1

(3-{2-[3-(1,4,5,6,-Tetrahydro-pyrimidin-2-ylamino)-phenyl]-acetyl}-2,3,4,4a,9,9a-hexahydro-1H-3-aza-fluoren-9-yl)-acetic acid, Cmpd 1

(3-{2-[3-(1,4,5,6,-Tetrahydro-pyrimidin-2-ylamino)-phenyl]-acetyl}-2,3,4,4a,9,9a-hexahydro-1H-3-aza-fluoren-9-yl)-acetic acid, Cmpd 2

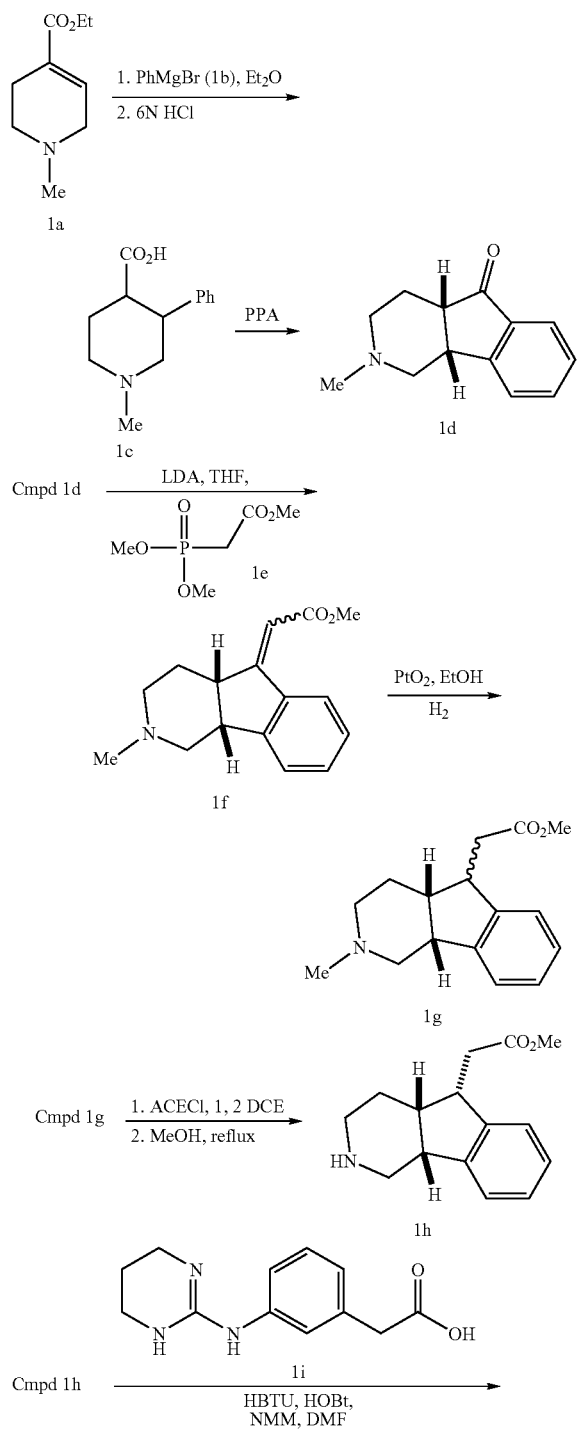

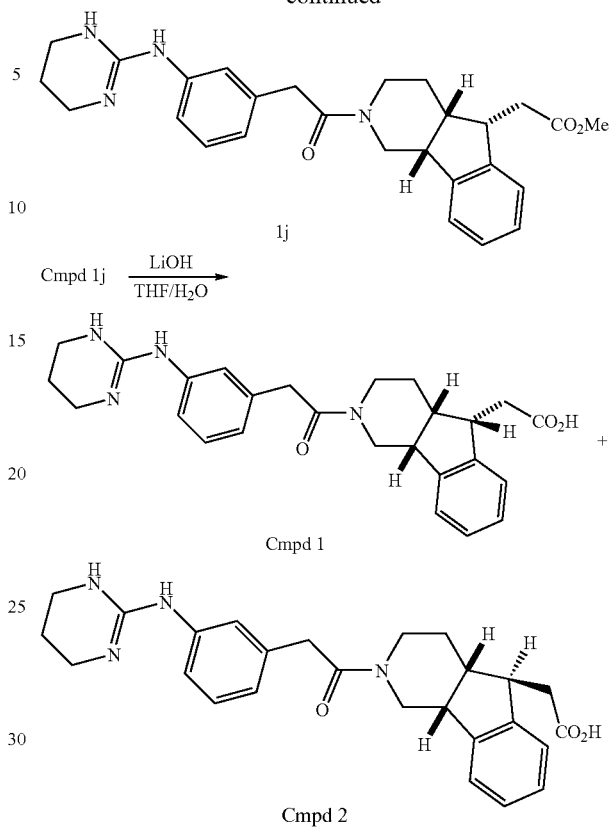

(Compound 1c was made by an adaptation of the procedure described in Paragamian, Vasken; U.S. Pat. No. 3,462,443, Aug. 19, 1969). A solution of 3 M phenylmagnesium bromide Compound 1b in diethyl ether (50 mL) was chilled to −10° C. before ethyl-1-methyl-1,2,3,6-tetrahydro-4-pyridine carboxylate Compound 1a (12 mL, 75 mmol) in diethyl ether (48 mL) was added dropwise over a 40 min period. The mixture continued to stir in an ice bath for 1 h and 20 min before the reaction was slowly poured into 200 mL of ice cold aqueous $NH_4Cl$ (ammonium chloride). The aqueous mixture was extracted with diethyl ether (2×100 mL). The organic layers were combined, dried over $MgSO_4$, filtered, and concentrated to give 17 g (92%) of a brown oil, which was used for the next step without further purification. MS (ES$^+$) m/z (relative intensity) 248.6 ((M+H)$^+$, 100), 289.5 ((M+H MeCN)$^+$, 60).

The brown oil was taken up in diethyl ether (100 mL) and washed with 6 N HCl (200 mL). The acidic layer was heated to 130° C. for 3 h, cooled to rt, and concentrated to a brown oil, which was taken up in MeCN and concentrated to give 17.22 g of a tan solid in a 98% yield of Compound 1c as the HCl salt. $^1$H NMR (CD$_3$OD, 300 MHz) δ 7.31-7.23 (m, 5H), 3.55 (t, 0.5H, J=5 Hz), 3.61-3.30 (m, 3.5H), 3.29-2.94 (m, 2H), 2.91 (s, 1.5H), 2.84 (s, 1.5H), 2.31-2.01 (m, 2H); $^{13}$C NMR (CD$_3$OD, 300 MHz) ppm 176.4, 140.0, 130.3, 129.4, 128.8, 59.6, 54.8, 46.5, 44.8, 42.9, 42.6, 28.6, 27.5; MS (ES$^+$) m/z (relative intensity) 220.2 ((M+H)$^+$, 100); Anal. Calcd for $C_{13}H_{17}NO_2$ 0.32$H_2O$ HCl: C, 60.18; H, 7.16; N, 5.72; Cl, 13.16; $H_2O$, 2.14; Found: C, 60.52; H, 7.25; N, 5.71; Cl, 13.54; $H_2O$, 2.51.

(Compound 1d was made by an adaptation of the procedure described in Paragamian, Vasken; U.S. Pat. No. 3,462, 443, Aug. 19, 1969). In a 500 mL three neck round bottom fitted with a mechanical stirrer, argon inlet, and stopper, polyphosphoric acid (PPA, 119 g) was heated to 80° C. for 1 h. The tan solid 1c (7.0 g, 28 mmol) was spooned in over a 10 min period and the heat was increased to 135° C. for 3 h. The thick solution was poured into ice water (300 mL) and the pH was adjusted to 13 with solid KOH. The basic solution was extracted with $CHCl_3$ (3×200 mL), and the extracts were combined, dried over $Na_2SO_4$, and concentrated. The crude brown oil was purified on $SiO_2$ using 95/5 $CH_2Cl_2$/MeOH to give 3.9 g (19 mmol, 68%) of Compound 1d as a light brown solid. $^1$H NMR ($CDCl_3$, 300 MHz) δ 7.77 (d, 1H, J=7 Hz), 7.56 (d, 1H, J=7 Hz), 7.47-7.36 (m, 2H), 3.36 (q, 1H, J=3 Hz), 3.08-3.03 (m, 2H), 2.79-2.74 (m, 1H), 2.60-2.57 (m, 2H), 2.22 (s, 3H), 2.01-1.88 (m, 2H). MS ($ES^+$) m/z (relative intensity) 248.6 ((M+H)$^+$, 100), 289.5 ((M+MeCN)$^+$, 60).

A solution of THF (40 mL) and trimethyl phosphonoacetate Compound 1e (3.9 mL, 24 mmol) was chilled to −78° C. before 2 M LDA in THF (9.7 mL, 19 mmol) was added dropwise. This solution was stirred at −78° C. for 30 min, warmed to rt, and heated to 40° C. for 1 h. The solution was allowed to come to room temperature before a solution of Compound 1d (2.44 g, 12.1 mmol) in THF (40 mL) was added over a 30 min period. The reaction mixture was heated to reflux for 24 h, cooled to rt, and concentrated under high vacuum. The brown oil was taken up in EtOAc (100 mL) and washed with 1 N NaOH (50 mL). The basic layer was washed with additional EtOAc (2×75 mL), and the organic layers were combined, washed 1 time with brine, dried over $Na_2SO_4$, and concentrated. The brown oil was purified on $SiO_2$ with (95:5) $CH_2Cl_2$/MeOH to give 2.02 g (7.86 mmol, 62%) of Compound 1f as a mixture of isomers (ratio 60/40). $^1$H NMR ($CDCl_3$, 300 MHz) δ 8.65 (d, 0.5H, J=8 Hz), 7.75 (d, 0.5H, J=8 Hz), 7.42-7.27 (m, 3H), 6.23 (s, 0.4H), 5.88 (s, 0.6H), 3.96-3.92 (m, 0.5H), 3.83-3.78 (m, 0.5H), 3.77 (s, 3H), 3.31-3.25 (m, 1H), 2.97 (q, 0.5H, J=5 Hz), 2.66 (q, 0.5H, J=5 Hz), 2.46-2.31 (m, 2H), 2.29 (s, 1.2H), 2.24 (s, 1.8H), 2.17-2.14 (m, 0.5H), 2.05-1.90 (m, 1H), 1.82-1.76 (m, 0.5H), 1.46-1.22 (m, 1H); $^{13}$C NMR ($CDCl_3$, 300 MHz) ppm 167.6, 166.9, 165.6, 161.3, 150.6, 149.0, 139.4, 137.3, 131.6, 131.1, 129.4, 127.4, 127.3, 123.7, 123.6, 122.9, 111.1, 107.9, 58.3, 55.2, 53.8, 53.1, 51.5, 51.4, 47.2, 46.8, 46.0, 43.1, 42.6, 41.8, 28.3, 27.7; MS ($ES^+$) m/z (relative intensity) 258.1 (M+H)$^+$, 100), 299.1 ((M+MeCN)$^+$, 20).

The hydrogenation of 1f (990 mg, 3.85 mmol) was carried out under 44 psi of $H_2$ with 20-mol % of $PtO_2$ (172 mg, 0.758 mmol) in EtOH (30 mL) over a 24 h period. The reaction was filtered through a pad of Celite, concentrated, and purified with $CH_2Cl_2$/MeOH (93/7) on $SiO_2$ to give (830 mg, 83%) of Compound 1g as a clear yellow oil. $^1$H NMR ($CDCl_3$, 300 MHz) δ 7.24-7.20 (m, 3H), 7.18 (d, 1H, J=4 Hz), 3.75 (s, 3H), 3.40 (d, 1H, J=10 Hz), 3.16 (t, 1H, J=10 Hz), 2.90 (d, 0.5H, J=6 Hz), 2.85 (d, 0.5H, J=6 Hz), 2.65 (d, 1H, J=7 Hz), 2.58-2.47 (m, 2H), 2.41-2.27 (m, 2H), 2.25 (s, 3H), 1.85 (t, 1H, J=2 Hz), 1.47-1.41 (m, 1H), 1.26-1.12 (m, 1H); MS ($ES^+$) m/z (relative intensity) 260.5 ((M+H)$^+$, 100), 301.3 ((M+MeCN)$^+$, 20).

Compound 1g (830 mg, 3.20 mmol) was dissolved in 1,2 dichloroethane (32 mL) and chilled to 4° C. before 1-chloroethyl chloroformate (ACE-Cl) (675 µL, 6.40 mmol) was added. The reaction mixture was stirred at 4° C. for 15 min and allowed to warm to rt before heating to reflux for 24 h. The solution was concentrated and the residue was dissolved in dry MeOH (32 mL). The heated mixture was concentrated to give 748 mg of Compound 1h (305 mmol, 95%) as a light tan solid which was used without further purification. $^1$H NMR ($CDCl_3$, 300 MHz) δ 7.35-7.23 (m, 3H), 7.12 (d, 1H, J=6 Hz), 3.76 (s, 3H), 3.75-3.67 (m, 2H), 3.44-3.40 (m, 2H), 2.93-2.82 (m, 3H), 2.52 (m, 1H), 1.87-1.26 (m, 4H); MS ($ES^+$) m/z (relative intensity) 246.1 ((M+H)$^+$, 100), 287.1 (M+MeCN)$^+$, 20); Anal. Calcd for $C_{15}H_{19}NO_2$: C, 59.20; H, 7.47; N, 4.37. Found: C, 59.19; H, 7.47; N, 4.03.

Compound 1h (217 mg, 0.813 mmol) was dissolved in DMF (5 mL) and treated with NMM (N-methylmorpholine) (178 µL, 1.63 mmol) before the mixture was chilled to 0° C. The reaction mixture was treated with 20-mol % of HOBt (1-hydroxybenzotriazole) (22 mg), and stirred in an ice bath for an additional 10 min, before a slurry of Compound 1i (200 mg, 0.813 mmol) and NMM (178 µL, 1.63 mmol) in DMF (5 mL) was added. The reaction mixture was stirred for 30 min at 0° C. and treated with HBTU (463 mg, 1.22 mmol). The reaction mixture was stirred for 36 h at rt, and the suspension was concentrated under high vacuum. Purification with $CH_2Cl_2$/MeOH (90/10) on $SiO_2$ gave 240 mg of Compound 1j (0.522 mmol, 64%) as a white solid. MS ($ES^+$) m/z (relative intensity) 461.5 ((M+H)$^+$, 100).

A mixture of $LiOH.H_2O$ (44.2 mg, 1.04 mmol) in $H_2O$ (3 mL) was added to a solution of Compound 1j (240 mg, 0.522 mmol) in THF (3 mL). This mixture was allowed to stir for 3 h at rt before the mixture was adjusted to a pH of 1 with TFA. The reaction mixture was concentrated, purified by Gilson Prep, and dried to give 142 mg of the enriched cis-Compound 1 (0.318 mmol, 60%) and 28.1 mg of the trans-Compound 2 (0.063 mmol, 12%). Cmpd 1: $^1$H NMR ($CD_3OD$, 300 MHz) δ 7.43-7.34 (m, 1H), 7.28-7.16 (m, 4H), 7.03 (t, 1H, J=8 Hz), 6.86-6.84 (m, 1H), 6.80 (s, 1H), 5.18 (d, 1H, J=14 Hz), 4.55 (d, 0.5H, J=14 Hz), 4.33 (d, 0.5H, J=13 Hz), 3.91-3.56 (m, 5H), 3.38 (bs, 5H), 3.17-3.03 (m, 2H), 2.89-2.78 (m, 2H), 2.41-2.32 (m, 1H), 2.00 (s, 2H), 1.42 (d, 1H, J=13 Hz), 0.78-0.67 (m, 1H). MS ($ES^+$) m/z (relative intensity) 447 ((M+H)$^+$, 100). Anal. Calcd for $C_{26}H_{30}N_4O_3$ 0.84 $H_2O$ 1.8 TFA: C, 53.25; H, 5.05; N, 8.39; F, 15.44; $H_2O$, 2.27 Found: C, 52.91; H, 4.75; N, 8.49; F, 15.09; $H_2O$, 1.98. HRMS ($FAB^+$) m/z Calcd for $C_{26}H_{31}N_4O_3$: 447.2396; Found 447.2403. Cmpd 2: $^1$H NMR ($CD_3OD$, 300 MHz) δ 7.43-6.88 (m, 9H), 4.39 (d, 1H, J=14 Hz), 3.9-3.34 (m, 10H), 330-3.21 (m, 2H), 2.61-2.40 (m, 2H), 2.00 (s, 2H), 1.85-1.78 (m, 1H), 1.76-1.61 (m, 1H), 1.32-1.25 (m, 1H); MS ($ES^+$) m/z (relative intensity) 447.2 ((M+H)$^+$, 100). HRMS ($FAB^+$) m/z Calcd for $C_{26}H_{31}N_4O_3$: 447.2396; Found 447.2409.

Using the procedure for Example 1, other compounds of the present invention may be prepared by those skilled in the art by varying the starting materials, reagent(s) and conditions used:

| Cmpd | MS (MH$^+$) |
|---|---|
| 3 | 434.3 |
| 4 | 420.3 |
| 5 | 463.4 |

Example 2

{3-[4-(Pyridin-2-ylamino)-butyryl]-2,3,4,4a,9,9a-hexahydro-1H-3-aza-fluoren-9-yl}-acetic acid, and

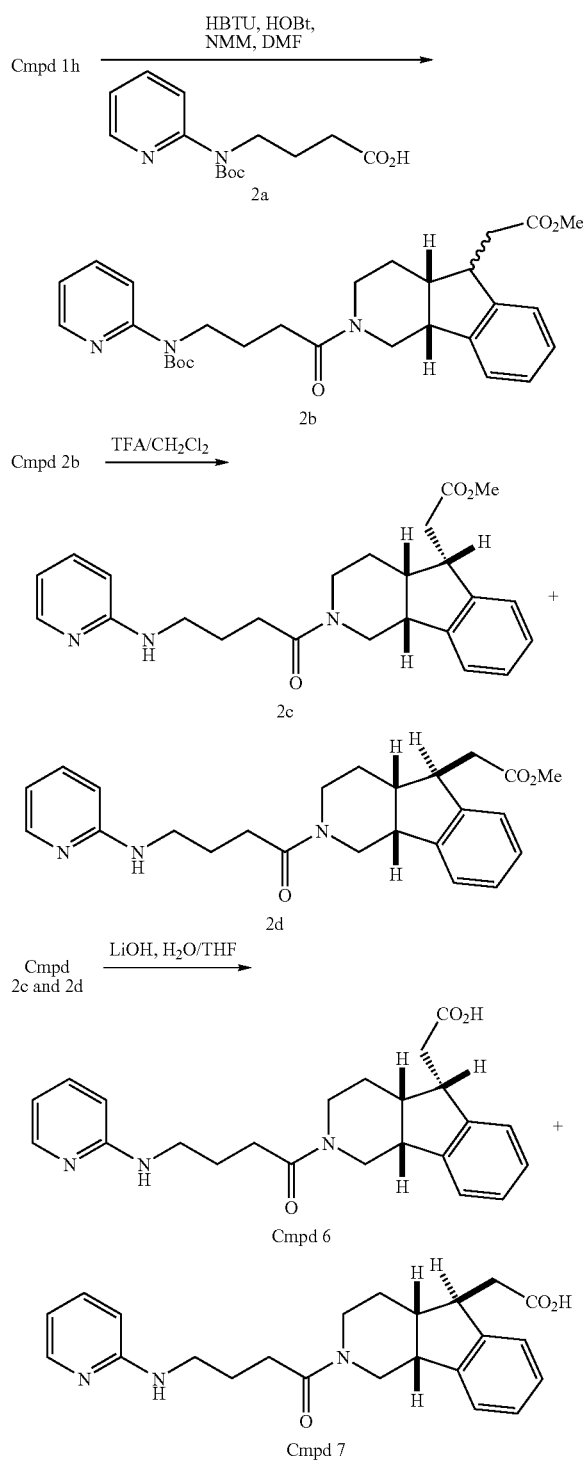

Compound 2b was synthesized using an adaptation of the procedure described for the synthesis of Compound 1j, substituting Compound 2a for Compound 1i.

Compound 2b (471 mg, 0.904 mmol) was dissolved in $CH_2Cl_2$ (5 mL) and TFA (5 mL). The reaction was stirred for 4 h and concentrated to a clear yellow oil. The crude material was purified on the Gilson prep, to give 283 mg of Compounds 2c/2d as the ester TFA salt (0.528 mmol, 60%) as a glass-like oil: $^1$H NMR (CDCl$_3$, 300 MHz) δ 7.86-7.83 (m, 2H), 7.32-7.19 (m, 4H), 6.90-6.87 (m, H), 6.80 (t, 1H, J=7 Hz), 5.19 (d, 0.5, J=14 Hz), 4.44 (t, 0.5H, J=13 Hz), 3.82-3.48 (m, 5H), 3.35-3.08 (m, 5H), 2.96-2.84 (m, 2H), 2.72-2.39 (m, 4H), 1.61 (bs, 4H), 1.11-1.07 (m, 1H); MS (ES$^+$) m/z (relative intensity) 422.2 ((M+H)$^+$, 100).

Compounds 6 and 7 were synthesized using an adaptation of the procedure described for the synthesis of Compounds 1 and 2, substituting Compounds 2c/2d for Compound 1j. Compound 6 (101 mg, 35%): $^1$H NMR (CD$_3$OD, 500 MHz) δ 7.80 (d, 1H, J=1 Hz), 7.35-7.06 (m, 5H), 6.94-6.77 (m, 2H), 5.16 (d, 1H, J=14 Hz), 4.46-4.35 (m, 0.5H), 4.19-4.00 (m, 1.5H), 3.75-3.54 (m, 2H), 3.21-2.97 (m, 2H), 2.94-2.60 (m, 3H), 2.53-2.33 (m, 2H), 2.28-2.23 (m, 1H), 2.10-1.90 (m, 2H), 1.63-1.58 (m, 2H), 0.99 (q, 1H, J=4 Hz); MS (ES$^+$) m/z (relative intensity) 394.4 ((M+H)$^+$, 100); HRMS (FAB$^+$) m/z Calcd for $C_{23}H_{27}N_3O_3$: 394.2131; Found 394.2119.

Compound. 7 (14 mg, 10%): $^1$H NMR (CD$_3$OD, 300 MHz) δ 7.91-7.84 (m, 1H), 7.32-7.06 (m, 6H), 6.88-6.81 (m, 1H), 4.30 (d, 0.5H, J=5 Hz), 4.26 (d, 0.5H, J=5 Hz), 4.07-3.96 (m, 2H), 3.78-3.57 (m, 3H), 3.49-3.34 (m, 4H), 2.89-2.34 (m, 4H), 2.05-1.93 (m, 3H), 1.56-1.48 (m, 1H); MS (ES$^+$) m/z (relative intensity) 394.4 ((M+H)$^+$, 100).

Using the procedure for Example 2, other compounds of the present invention may be prepared by those skilled in the art by varying the starting materials, reagent(s) and conditions used:

| Cmpd | MS (MH$^+$) |
|---|---|
| 8 | 408.2 |

Example 3

[2-(4-5,6,7,8-Tetrahydro-[1,8]naphthyridine-2-yl-butyryl)-2,3,4,4a,9,9a-hexahydro-1H-indeno[2,1-c]pyridin-9-yl]-acetic acid, Cmpd 9 and Cmpd

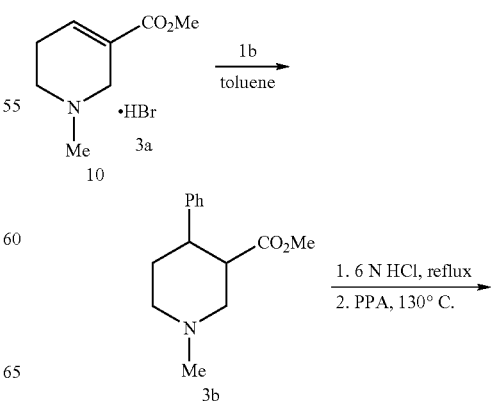

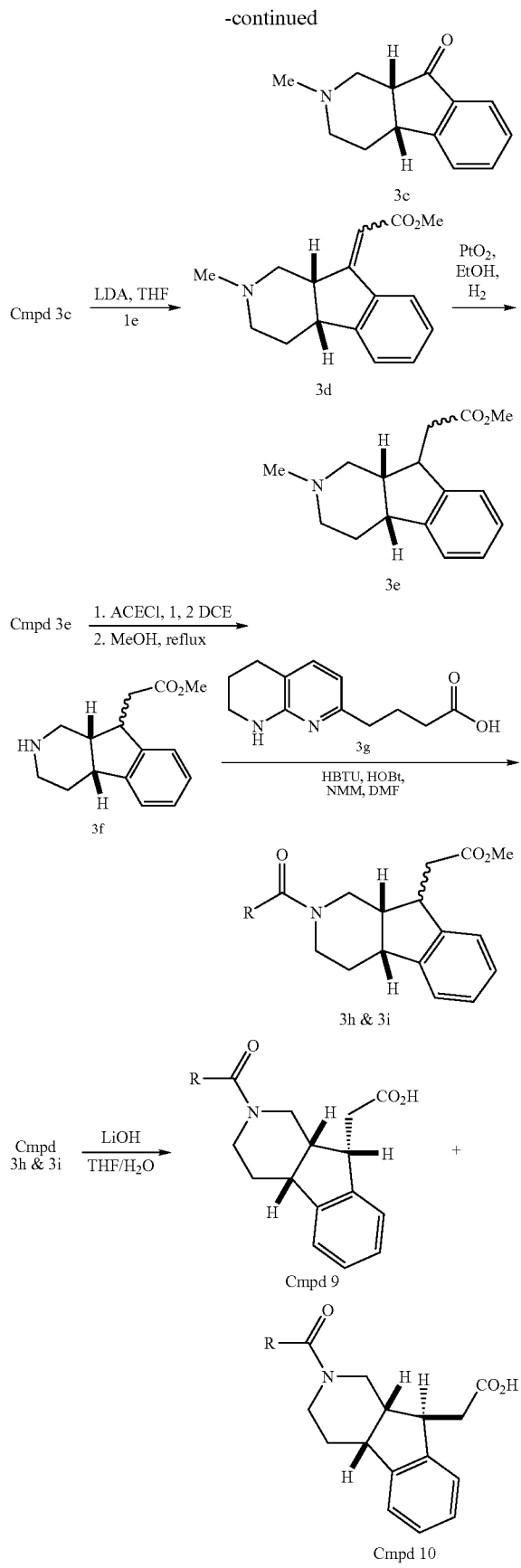

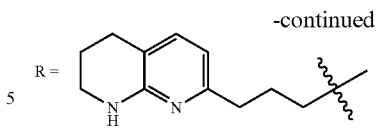

Arecoline hydrobromide Compound 3a (2.06 g, 8.73 mmol) was dissolved in toluene (40 mL) and chilled to −10° C. Sodium hydride (239 mg of 90%, 9.70 mmol) was slowly added to the solution while maintaining the temperature at −10° C. After stirring for 15 min, a 3 M solution of Compound 1b in Et$_2$O (6 mL) was added dropwise. The reaction mixture was stirred at −10° C. for 1 h then treated with 2 N HCl (200 mL) to neutralize. The reaction mixture was poured into toluene (100 mL) and made basic with K$_2$CO$_3$. The basic layer was extracted with toluene (3×), dried over Na$_2$SO$_4$, and concentrated. The crude reaction mixture was purified by SiO$_2$ chromatography with CH$_2$Cl$_2$/MeOH (9:1) to give 1.74 g of Compound 3b (7.25 mmol, 83%) as a clear yellow oil. $^1$H NMR (CDCl$_3$, 300 MHz)δ 7.31-7.19 (m, 5H), 3.74 (s, 3H), 3.19-3.18 (m, 3H), 3.05-2.95 (m, 3H), 2.42 (s, 3H), 1.88-1.84 (m, 2H); MS (ES$^+$) m/z (relative intensity) 234.2 ((M+H)$^+$, 100).

Compound 3b (1.74 g, 7.25 mmol) was taken up in 6 N HCl (25 mL) and heat to 130° C. for 17 h. The reaction mixture was cooled, concentrated, and dried overnight to give 1.30 g (80%) of the free acid as a white solid. $^1$H NMR (CD$_3$OD, 300 MHz) δ 7.32-7.07 (m, 5H), 3.80-3.59 (m, 3H), 3.43-3.06 (m, 3H), 3.00 (s, 3H), 2.67-2.58 (m, 2H); MS (ES$^+$) m/z (relative intensity) 220.0 ((M+H)$^+$, 100).

In a 500 mL three neck round bottom flask fitted with a mechanical stirrer, argon inlet, and stopper PPA (40 g) was heated to 110° C. for 1 h. The free acid of Compound 3b, from above, was spooned into the hot PPA and the heat was increased to 130° C. The reaction mixture was allowed to stir at 130° C. for 4 h, before cooling to room temperature. The reaction mixture was poured into ice-cold water, and solid KOH was added until pH 10 was achieved. The basic layer was extracted with CHCl$_3$ (3×500 mL) and the organic layers were combined, washed with brine (500 mL), dried over Na$_2$SO$_4$, and concentrated to give Compound 3c as a brown oil (1.1 g, 75%) which was used without further purification for later reactions. $^1$H NMR (CDCl$_3$, 500 MHz) δ 7.68 (d, 1H, J=7 Hz), 7.57 (t, 1H, J=7 Hz), 7.48 (d, 1H, J=7 Hz), 7.36 (t, 1H, J=7 Hz), 3.58 (q, 1H, J=7 Hz), 3.31 (d, 1H, J=7 Hz), 2.73-272 (m, 1H), 2.55-2.40 (m, 2H), 2.19 (s, 3H), 2.16-1.96 (m, 2H), 1.47-1.35 (m, 1H); $^{13}$C NMR (CDCl$_3$, 500 MHz) ppm 204.6, 156.5, 126.5, 123.8, 123.3, 1134.3, 113.4, 52.4, 52.0, 48.0, 45.4, 35.0, 30.7; MS (ES$^+$) m/z (relative intensity) 202.1 ((M+H)$^+$, 100), 203.1 ((M+2H)$^+$, 30).

An argon-blanketed solution of THF (40 mL) and Compound 1e (1.7 mL, 11 mmol) was chilled to −78° C. for 45 min before 2 M LDA in THF (4.0 mL, 8.0 mmol) was added dropwise. The reaction mixture was stirred at −78° C. for 10 min, warmed to rt for 1 h, and heated to 60° C. for 30 min. A solution of Compound 3c (1.1 g, 5.47 mmol) in THF (40 mL) was added to the reaction mixture at rt, and heated to reflux for 24 h. The concentrated mixture was taken up in EtOAc (100 mL), washed with 1 N NaOH (3×50 mL), brine (50 mL), dried over Na$_2$SO$_4$ and concentrated. Purification by SiO$_2$ chromatography with CH$_2$Cl$_2$/MeOH (94:6) gave Compound 3d (300 mg, 22%) of diastereomer ratio of (7:3) as clear oil. $^1$H NMR (CDCl$_3$, 300 MHz) δ 8.67 (d, 0.5H, J=8 Hz), 7.76 (d, 0.5, H, J=8 Hz), 7.57-7.27 (m, 3H), 6.25

(s, 0.3H), 5.94 (s, 0.7H), 4.27-4.18 (m, 0.3H), 3.78 (s, 0.9H), 3.76 (s, 2.1H), 3.41-3.12 (m, 2.7H), 2.85-278 (m, 0.7H), 2.68-2.62 (m, 1H), 2.60-2.46 (m, 2H), 2.19 (s, 3H), 2.10-1.83 (m, 2.3H), 1.80-1.71 (m, 0.7H); HPLC $R_f$=4.84 (70%) & 5.13 (30%) 0-30.

Hydrogenation of Compound 3d (300 mg, 1.17 mmol) was carried out under 44 psi of $H_2$ with 20 mol % of $PtO_2$ (80 mg, 0.35 mmol) in EtOH (18 mL) over a 24 h period. The reaction was filtered, concentrated, and purified with $CH_2Cl_2$/MeOH (93/7) on $SiO_2$ to give 300 mg of Compound 3e (98%) as a clear yellow oil. $^1$H NMR ($CDCl_3$, 300 MHz) δ 7.32-7.14 (m, 4H), 3.78 (s, 1.5H), 3.71 (s, 1.5H), 3.29-3.27 (m, 2H), 2.99-2.45 (m, 4H), 2.36 (s, 1.5H), 2.33 (s, 1.5H), 2.26-2.04 (m, 2H), 1.67-1.12 (m, 2H), 0.95-0.84 (m, 1H); MS ($ES^+$) m/z (relative intensity) 260.5 (($M+H$)$^+$, 100).

Compound 3e (300 mg, 1.17 mmol) was dissolved in 1,2-dichloroethane (12 mL) and chilled to 4° C. in an ice bath before ACE-Cl (495 µL, 4.68 mmol) was added. The reaction mixture was stirred at 4° C. for 15 min and allowed to warm to rt before heating to reflux for 36 h. The solution was cooled, concentrated, and the residue was dissolved in dry MeOH (32 mL) and heated to 50° C. for 2 h. The reaction mixture was cooled to rt and concentrated to give 264 mg of Compound 3f as a light tan solid which was used for later reactions without further purification.

Compound 3g (264 mg, 1.17 mmol) was dissolved in DMF (10 mL) and 3 equivalents of NMM (385 µL, 3.51 mmol) was added. The reaction mixture was chilled to 4° C. and treated with HOBt (33 mg, 20 mol %). The reaction mixture was stirred for an additional 30 min before a solution of Compound 3f (287 mg, 1.17 mmol) in DMF (10 mL), and NMM (385 µL, 3.51 mmol) was added. This reaction mixture was allowed to stir for 30 min in an ice bath before treating with HBTU (666 mg, 1.76 mmol). The solution stirred in an ice bath for 1.5 h before pouring the mixture into 1 N NaOH (40 mL) and EtOAc (50 mL). The organic layer was washed with 1 N NaOH (3×50 mL), dried with $Na_2SO_4$ and concentrated. The purification was carried out on the Gilson Prep using 30 to 90 (MeCN/$H_2O$). A total of 300 mg of Compounds 3h & 3i (0.671 mmol, 57%) was recovered as a mixture of diastereomers (ratio 1:1) as a clear oil. $^1$H NMR ($CDCl_3$, 300 MHz) δ 7.34-7.19 (m, 6H), 6.49 (t, 1H, J=3 Hz), 4.51-4.29 (m, 0.5H), 3.83 (s, 1.5H), 3.75 (s, 1.5H), 3.57-3.30 (m, 5.5H), 2.83-2.49 (m, 11H), 2.14-1.97 (m, 6H) MS ($ES^+$) m/z (relative intensity) 448.4 (($M+H$)$^+$, 100).

Compound mixture 3h & 3i (0.671 mmol) was taken up in THF/$H_2O$ (12 mL) (1:1) and treated with LiOH.$H_2O$ (141 mg, 3.36 mmol) at 4° C. Upon completion after 1.5 h, the reaction was acidified with TFA to pH 1 and concentrated. The crude material was purified on the Gilson prep with MeCN/$H_2O$ 20 to 90% to give Compound 9 (105 mg, 36%) and Compound 10 (108 mg, 37%).

Compound 9: $^1$H NMR ($CDCl_3$, 300 MHz) δ 13.8 (bs, 1H) 7.37 (d, 0.5H, J=7 Hz), 7.26-7.14 (m, 5H), 6.47 (d, 0.5H, J=7 Hz), 4.37 (d, 1H, J=13 Hz), 3.86 (d, 1H, J=13 Hz), 3.61-3.50 (m, 4H), 3.34 (bs, 2H), 3.14 (d, 0.5H, J=5 Hz), 3.09 (d, 0.5H, J=5 Hz), 3.00-1.94 (m, 13H); MS ($ES^+$) m/z (relative intensity) 434.1 (($M+H$)$^+$, 100). HPLC, $R_f$=3.080 at 220 nm; HRMS ($FAB^+$) m/z Calcd for $C_{26}H_{32}N_3O_3$: 434.244367; Found 434.243593.

Compound 10: $^1$H NMR ($CDCl_3$, 300 MHz). δ 7.37 (d, 0.5H, J=8 Hz), 7.29-7.21 (m, 5H), 6.46 (d, 0.5H, J=8 Hz), 3.73-3.63 (m, 1H), 3.52-3.22 (m, 6H), 3.14 (d, 0.5H, J=5 Hz), 3.09 (d, 0.5H, J=5 Hz), 2.80-2.71 (m, 4H), 2.58-2.39 (m, 4H), 2.06-1.94 (m, 5H)), 1.62-1.59 (m, 1H); MS ($ES^+$) m/z (relative intensity) 434.1 (($M+H$)$^+$, 100); HPLC, $R_f$=3.025 at 220 nm, HRMS ($FAB^+$) m/z Calcd for $C_{26}H_{32}N_3O_3$: 434.2444; Found 434.2436.

Using the procedure for Example 3, other compounds of the present invention may be prepared by those skilled in the art by varying the starting materials, reagent(s) and conditions used:

| Cmpd | MS (MH$^+$) |
|---|---|
| 11 | 420.2 |

Example 4

[2-(3-5,6,7,8-Tetrahydro-[1,8]naphthyrin-2-yl-propionyl)-1,2,3,3a,8,8a-hexahydro-2-aza-cyclopenta[a]inden-8-yl]-acetic acid, Cmpd 13 and 14

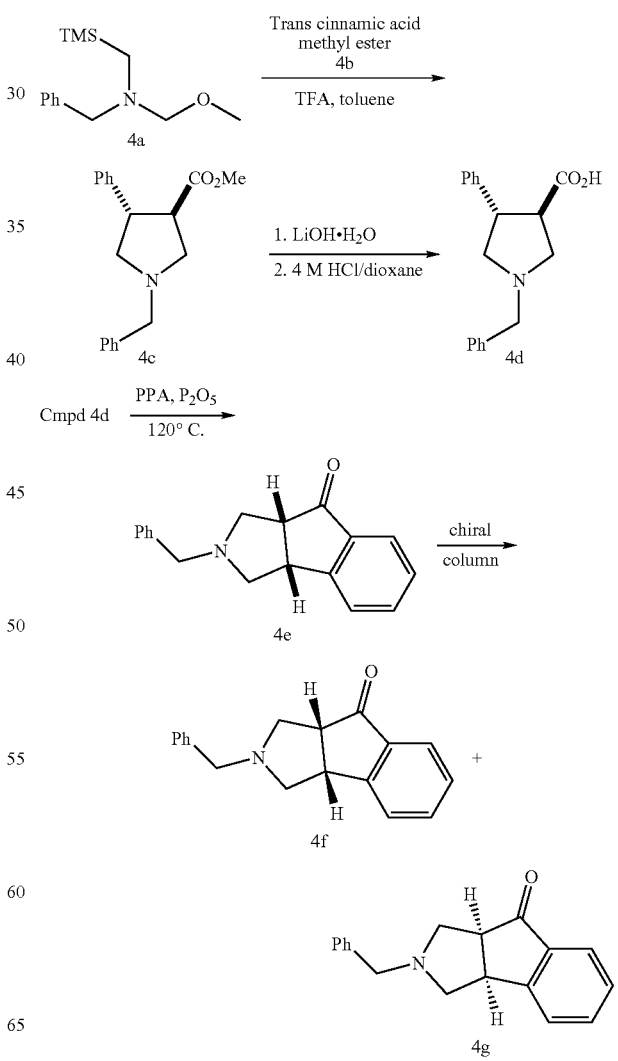

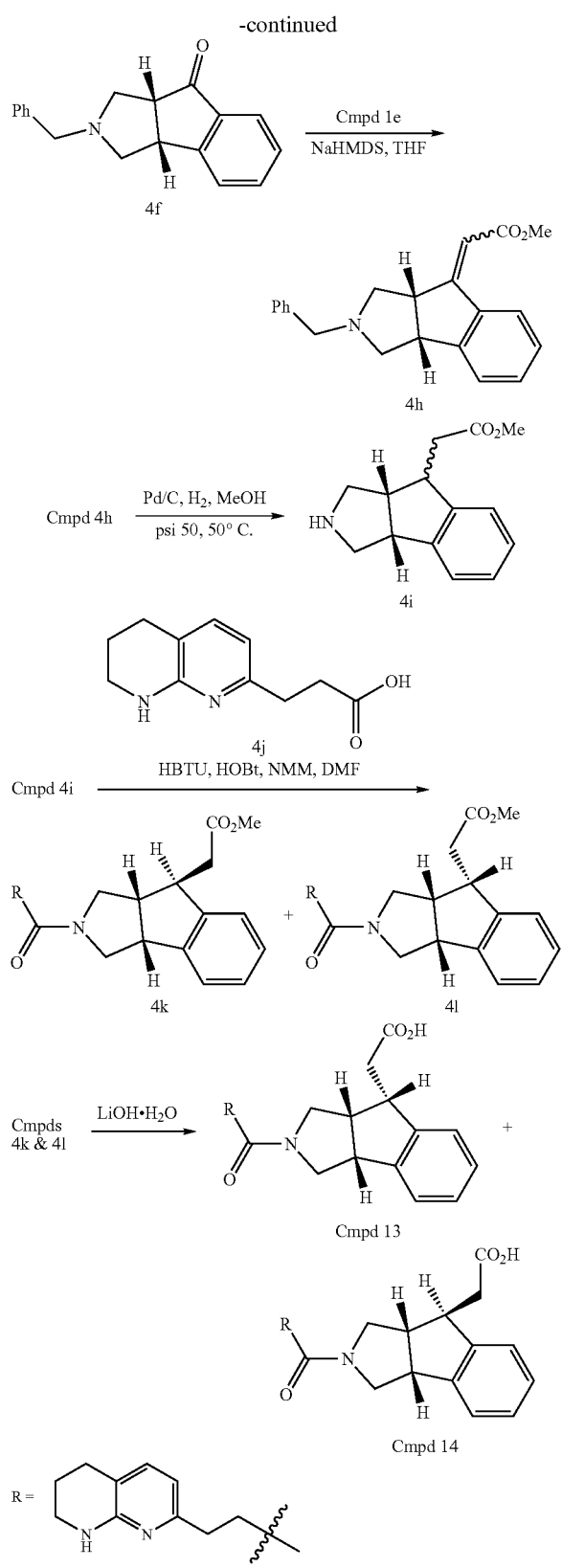

Benzyl-methoxymethyl-trimethylsilanylmethyl-amine Compound 4a (36 g, 0.152 mol) and trans-cinnamic acid methyl ester Compound 4b (25 g, 0.154 mol) were added to toluene (500 mL). Trifluoroacetic acid (5 g, 0.044 mol) was carefully added to the mixture in 1 g portions. Caution: EXOTHERMIC reaction. The entire quantity of TFA was added within 30 min. The reaction was stirred for 5 h, quenched with saturated NaHCO$_3$ solution (400 mL), and extracted with EtOAc (2×500 mL). The organic layers were combined and washed with water (500 mL), brine (500 mL), dried over Na$_2$SO$_4$, and concentrated at 150° C., 200 mTorr to give 10 g of Compound 4c (22%) as a clear oil. $^1$H NMR (300 MHz CDCl$_3$) δ 7.3-7.1 (m, 10H), 3.8-3.7 (m, 3H), 3.6 (s, 3H), 3.1-3.0 (m, 3H), 2.9-2.8 (m, 1H), 2.8-2.7 (m, 1H); $^{13}$C NMR (CDCl$_3$, 300 MHz) ppm 174.8, 144.5, 139.0, 128.9, 128.8, 128.6, 127.7, 127.3, 126.8, 62.2, 60.3, 57.9, 52.3, 52.1, 47.4; MS (ES$^+$) m/z (relative intensity) 296.3 ((M+H)$^+$, 100); Anal. Calcd for C$_{19}$H$_{21}$NO$_2$: C, 77.26; H, 7.17; N, 4.74; Found: C, 77.26; H, 7.49; N, 4.82.

Compound 4c (2.06 g, 6.98 mmol) was dissolved in THF/H$_2$O (100 mL, 1:1) to 4° C. and treated with LiOH.H$_2$O (0.89 g, 21 mmol). The reaction mixture was stirred for 2 h at 4° C. and acidified with concentrated HCl to pH 1. The solids were filtered, and the filtrate was concentrated to give Compound 4d as a white solid (2.0 g) in a quantitative yield. The Compound 4d was used without further purification. $^1$H NMR (300 MHz CDCl$_3$) δ 7.65-7.63 (m, 1H), 7.41-7.30 (m, 9H), 4.57 (s, 2H), 3.88-3.80 (m, 4H), 3.32-3.30 (m, 2H); MS (ES$^+$)/z (relative intensity) 282.1 ((M+H)$^+$, 100).

PPA (60 g), and P$_2$O$_5$ (6 g) were heated together in a 3-neck flask fitted with a mechanical stirrer, argon inlet, and stopper, to 100° C. for 1 h. Compound 4c (2.0 g, 7.0 mmol) was spooned in over a 10 min period and the heat increased to 130° C. for 3 h. The thick solution was poured into ice cool water (300 mL) and the pH was adjusted to 13 with solid KOH. The basic solution was extracted with CHCl$_3$ (3×200 mL), the combined extracts were dried over Na$_2$SO$_4$, and concentrated to give 1.3 g of Compound 4e (70%) as a brown oil. The enantiomers of Compound 4e were separated by a chiral column: Chiralpak® AD, Amylose tris-(3,5-dimethylphenylcarbamate) coated on a 20 μm silica-gel, 500 g; 5 cm ID; 41 cm length and as eluent using an isocratic mixture of hexane/ethanol: 80/20 vol/vol % at 80 mL/min.; wavelength 220 nM. Enantiomer 4f (first eluting compound) had an α$_{[D]}$=+14 and enantiomer 4g had an α$_{[D]}$=−14; $^1$H NMR (300 MHz CDCl$_3$) δ 7.63 (d, 1H, J=8 Hz), 7.50 (d of d, 1H, J=7.7 & 7.0 Hz), 7.39-6.85 (m, 7H), 3.70 (t, 1H, J=7.0 Hz), 3.44 (s, 2H), 3.12 (d, 1H, J=9.0 Hz), 3.00 (d of d, 1H, J=8.0 Hz & J=7.0 Hz), 2.83 (d, 1H, J=9 Hz), 2.54 (t, 1H, J=17 Hz), 2.42 (t, 1H, J=17 Hz); HPLC R$_f$=2.444 min, 220 nm & 254 nm; MS (ES$^+$)/z (relative intensity) 264.1 ((M+H)$^+$, 100).

A solution of THF (50 mL) and Compound 1e (2 mL, 12 mmol) was chilled to 0° C. before 1 M NaHMDS in THF (12 mL, 12 mmol) was added dropwise. This solution was stirred at 0° C. for 30 min, then allowed to warm to rt before adding Compound 4f (1.04 g, 3.80 mmol) in THF (40 mL) dropwise over a 30 min period. The reaction mixture was heated to reflux for 36 h, cooled to rt, and concentrated under high vacuum. The brown oil was taken up in EtOAc (100 mL), washed with 1 N NaOH (50 mL) and separated. The basic layer was extracted with EtOAc (2×75 mL) and the organic layers were combined, washed with brine, dried over Na$_2$SO$_4$, and concentrated. The brown oil was purified on SiO$_2$ with (70:30) Hexanes/EtOAc to give Compound 4h (1.01 g, 84%) of as a mixture of E,Z-isomers (ratio 1:1). $^1$H A 4-neck flask was fit with a mechanical stirrer, thermowell, stopper and nitrogen inlet all placed in a secondary container filled with tap water to be used as a heat sink.

NMR (CDCl$_3$, 300 MHz) δ 7.68 (d, 1H, J=7 Hz), 7.50 (m, 1H), 7.40-7.31 (m, 2H), 7.22-7.06 (m, 5H), 6.27 (s, 0.5H), 5.83 (s, 0.5H), 3.70 (s, 1.5H), 3.69 (s, 1.5H), 3.78-3.69 (overlapping m, 1H), 3.47 (s, 2H), 3.16 (d, 1H, J=9.0 Hz), 3.01 (m, 1H), 2.88 (d, 1H, J=9 Hz), 2.62-2.48 (m, 2H); HPLC R$_f$=3.202 min, 220 nm; MS (ES$^+$) m/z (relative intensity) 320.2 ((M+H)$^+$, 100).

Compound 4h (1.01 g, 3.20 mmol) was taken up in MeOH (40 mL), and 5% Pd/C (140 mg) was added. The reaction mixture was placed under 40 psi of H$_2$ and heated to 50° C. for 24 h. The reaction mixture was cooled to rt and filtered through a pad of Celite®. The filtrate was concentrated and placed under high vacuum overnight to dry. Compound 4i was used without further purification (720 mg, 98%). MS (ES$^+$) m/z (relative intensity) 232.0 ((M+H)$^+$, 100).

Compound 4j (760 mg, 3.13 mmol) was dissolved in DMF (20 mL) and 3 equivalents of NMM (1.03 mL, 9.39 mmol) was added. The reaction mixture was chilled to 4° C. and HOBt (86 mg) was added. The reaction mixture was stirred for an additional 30 min before a solution of Compound 4i (720 mg, 3.13 mmol) and NMM (1.03 mL, 9.39 mmol) in DMF (20 mL) was added. The reaction mixture was allowed to stir for 30 min in an ice bath before treating with HBTU (1.78 g, 4.70 mmol). The solution was stirred in an ice bath for 3 h before pouring the mixture into 1 N NaOH (50 mL), and EtOAc (50 mL). The organic layer was separated and washed with 1 N NaOH (3×50 mL), dried with Na$_2$SO$_4$ and concentrated. The compound was purified on the Gilson Prep 15 to 90% (MeCN) gradient. The ester Compounds 4k and 4l (600 mg, 1.43 mmol) was recovered as a mixture of diastereomers (ratio 1:1) in a 46% yield as a clear oil. $^1$H NMR (CDCl$_3$, 300 MHz) δ 7.33-7.13 (m, 5H), 6.49-6.43 (m, 1H), 4.11-3.97 (m, 2H), 3.77 (s, 3H), 3.49 (bs, 2H), 3.29 (t, 0.5H, J=17 Hz), 3.13 (t, 0.5H, J=17 Hz), 2.99-2.83 (m, 3H), 2.79-2.62 (m, 3H) 2.60-2.43 (m, 2H), 1.93 (bs, 2H); MS (ES$^+$) m/z (relative intensity) 420.1 ((M+H)$^+$, 100).

Ester Compounds 4k and 4l (600 mg, 1.43 mmol) were dissolved in THF/H$_2$O (30 mL, 1:1) and treated with LiOH.H$_2$O (300 mg, 7.15 mmol). The reaction mixture was stirred for 1 h and quenched with TFA to adjust to pH 0.1. The acid was purified using 10:90 (MeCN/H$_2$O) to give Compounds 13 and 14 (545 mg, 73%, ratio of diastereomers 1:1) as the TFA salt. $^1$H NMR (CD$_3$OD, 500 MHz) δ 7.51-7.44 (m, 1H), 7.29-7.21 (m, 4H), 6.56-6.49 (m, 1H), 3.97-3.63 (m, 5H), 3.45 (bs, 3H), 3.27 (t, 0.5H, J=13 Hz), 3.14 (t, 0.5H, J=11 Hz), 3.03-2.85 (m, 4H), 2.79-2.44 (m, 5H), 1.94-1.89 (m, 2H); $^{13}$C NMR (CD$_3$OD, 500 MHz) ppm 176.1, 172.1, 152.4, 148.8, 145.8, 142.6, 130.2, 129.1, 128.8, 126.1, 125.6, 124.9, 120.8, 111.7, 53.0, 47.6, 46.5, 42.2, 33.8, 33.6, 28.6, 26.4; HPLC R$_f$=2.794 min, 220 nm; MS (ES$^+$) m/z (relative intensity) 406.4 ((M+H)$^+$, 100); HRMS (FAB$^+$) m/z Calcd for C$_{24}$H$_{28}$N$_3$O$_3$: 406.2126; Found 406.2131.

The pair of diastereomers Compound 13 and 14 were separated using a Chiralpak® OD column, Cellulose tris-(3,5-dimethylphenylcarbamate) coated on a 20 μm silica-gel, 500 g; 5 cm ID; 41 cm length and as eluent using an isocratic mixture of hexane (+5% ethanol+0.1% TFA+0.02% TEA)/methanol/ethanol: 85/9.75/5.25 vol/vol/vol % at 80 mL/min and a wavelength 215 nM. The optical rotation of Compound 13 first eluting [α]$_D$=−18.2 and Compound 14 [α]$_D$=+18.7. Using the procedure for Example 4, other compounds of the present invention may be prepared by those skilled in the art by varying the starting materials, reagent(s) and conditions used:

| Cmpd | MS (MH$^+$) |
|------|-------------|
| 12   | 406.4       |
| 15   | 420.4       |
| 16   | 424.2       |

Example 5

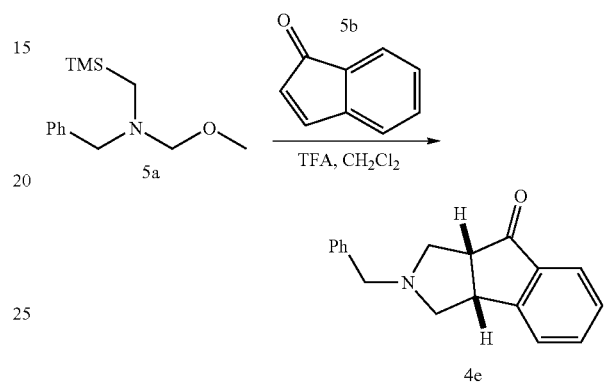

Compound 4e was prepared by an alternate method as described below, and was subsequently converted into Compounds 12-16 following the procedure provided in Example 4.

To a solution of Compound 5a (1.6 g, 6.9 mmol) in CH$_2$Cl$_2$ at 0° C. was added Compound 5b (Prepared in one step from indanone: Nicolaou, K. C.; Montagnon, T.; Baran, P. S. Angewandte Chemie, Intl. Ed. 2002, 41(8), 1386-1389) (750 mg, 5.8 mmol) in CH$_2$Cl$_2$, followed by TFA (0.5 mL, 1 M solution in CH$_2$Cl$_2$). The reaction was allowed to warm to rt and stirred overnight. The solution was quenched with saturated sodium bicarbonate and then washed with brine. The organic layer was dried over Na$_2$SO$_4$ and the solvent removed to give a yellow oil. Purification using Biotage 40S (8:1 heptanes/EtOAc) provided Compound 4e (470 mg, 31%) as a light yellow oil. Anal. Calcd for C$_{18}$H$_{17}$NO-0.5H$_2$O: C, 79.38; H, 6.66; N, 5.14. Found: C, 79.67; H, 6.59; N, 5.31.

Biological Experimental Example

As demonstrated by biological studies described hereinafter, as shown in Table II, the compounds of the present invention are αvβ3 and αvβ5 integrin receptor antagonists useful in treating an integrin mediated disorder.

Example 1

In Vitro Solid Phase Purified αvβ3 Binding Assay

The vitronectin/αvβ3 binding assay methods were derived from Mehta et al. (*Biochem J*,. 1998, 330, 861). Human αvβ3 (Chemicon International Inc., Temecula, Calif.), at a concentration of 1 μg/ml dissolved in Tris buffer (20 mM Tris, 1 mM CaCl$_2$, 1 mM MgCl$_2$, 10 μM MnCl$_2$, 150 mM NaCl), was immobilized on Immulon 96 well plates (Dynex Technologies, Chantilly, Va.) overnight at 4° C. Plates were washed and treated with blocking buffer (3%

BSA in Tris buffer) for 2 h at 37° C. Plates were then rinsed 2 times with assay buffer comprised of Tris buffer. Synthesized compounds were added to wells in duplicate immediately prior to the addition of 2 nM vitronectin (Sigma, St. Louis, Mo.). Following a 3 hour incubation at 37° C., plates were washed 5 times in assay buffer. An anti-human vitronectin IgG rabbit polyclonal antibody (Calbiochem, San Diego, Calif.) was added (1:2000) and plates were incubated for 1 hour at room temperature. VectaStain ABC peroxidase kit reagents (Vector Laboratories, Burlingame, Calif.) employing a biotin labeled anti-rabbit IgG, were utilized for detection of bound antibody. Plates were read at 490 nm on a Molecular Devices (Sunnyvale, Calif.) microplate reader. Table 1 shows the results of the in vitro solid phase purified $\alpha v\beta 3$ binding assay for representative compounds of the present invention.

purified GP IIb/IIIa binding assay for representative compounds of the present invention.

Example 3

In Vitro Solid Phase Purified $\alpha v\beta 5$ Binding Assay

The vitronectin/$\alpha_V\beta_5$ binding assay method was performed in the same manner as the vitronectin/$\alpha_V\beta_3$ binding assay of Example 2, with the difference that 1 µg/mL of human purified $\alpha_V\beta_5$ (Chemicon International, Inc.) was immobilized onto Immulon 96 well plates (Dynex Technologies) instead of $\alpha_V\beta_3$. All other aspects of the assay including buffers, reagents and incubation times remain unchanged.

TABLE II

| | | | Antagonist IC$_{50}$ Activity (nM) | | | | | |
|---|---|---|---|---|---|---|---|---|
| Racemic mixtures | | | (cis) diastereomer | | | (trans) diastereomer | | |
| Cpd | $\alpha_V\beta_3$ | $\alpha_V\beta_5$ | Cpd | $\alpha_V\beta_3$ | $\alpha_V\beta_5$ | Cpd | $\alpha_V\beta_3$ | $\alpha_V\beta_5$ |
| | | | 1 | 66 ± 6 | 1020 ± 180 | 2 | 126 ± 40 | 217 ± 5 |
| 3 | 85 ± 8 | 230 ± 40 | | | | | | |
| 4 | 87 | 189 | | | | | | |
| 5 | 371 | NT | | | | | | |
| | | | 6 | >1 | NT | 7 | >1 | NT |
| 8 | 46% @ 1 µM | NT | | | | | | |
| | | | 9 | 41% @ 50 µM | NT | 10 | 51% @ 50 µM | |
| 11 | >1 | NT | | | | | | |
| 12 | 26 ± 8 | 15 ± 2 | 13* | 290 ± 90 | 260 ± 60 | 14* | 17 ± 3 | 5.8 ± 1.2 |
| 15 | 411 | 538 | | | | | | |
| 16 | 188 ± 50 | 70 ± 20 | | | | | | |

*enantiomers

Example 2

In Vitro Solid Phase Purified GP IIb/IIIa Binding Assay A 96 well Immulon-2 microtiter plate (Dynatech-Immulon) was coated with 50 µL/well of RGD-affinity purified GP IIb/IIIa (effective range 0.5-10 µg/mL) in 10 mM HEPES, 150 mM NaCl, 1 mM MgCl$_2$ at pH 7.4. The plate was covered and incubated overnight at 4° C. The GP IIb/IIIa solution was discarded and 150 µL of 5% BSA was added and incubated at RT for 1-3 h. The plate was washed extensively with modified Tyrodes buffer. Biotinylated fibrinogen (25 µL/well) at 2× final concentration was added to the wells that contain the test compounds (25 µL/well). The plate was covered and incubated at RT for 2-4 h. Twenty minutes prior to incubation completion, one drop of Reagent A (VectaStain ABC Horseradish Peroxidase kit, Vector Laboratories, Inc.) and one drop Reagent B were added with mixing to 5 mL modified Tyrodes buffer mix and let stand. The ligand solution was discarded and the plate washed (5×200 µL/well) with modified Tyrodes buffer. Vecta Stain HRP-Biotin-Avidin reagent (50 µL/well, as prepared above) was added and incubated at RT for 15 min. The Vecta Stain solution was discarded and the wells washed (5×200 µL/well) with modified Tyrodes buffer. Developing buffer (10 mL of 50 mM citrate/phosphate buffer @ pH 5.3, 6 mg o-phenylenediamine, 6 µL 30% H$_2$O$_2$; 50 µL/well) was added and incubated at RT for 3-5 min and then 2 N H$_2$SO$_4$ (50 µL/well) was added. The absorbance was read at 490 nM. Table 1 shows the results of the in-vitro solid phase

What is claimed is:

1. A compound of Formula (I):

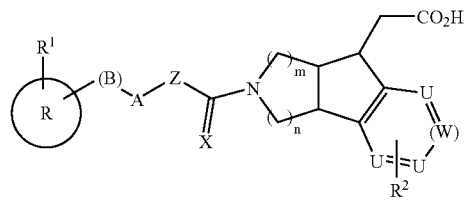

wherein:

R is selected from the group consisting of hetercyclyl and heteroaryl;

$R^1$ is one to two substituents selected from the group consisting of hydrogen, $C_{1-4}$alkyl, $C_{1-4}$alkoxy, hydroxy, —$NR^AR^B$, and halogen;

wherein alkyl and alkoxy are optionally substituted on a terminal carbon one to three substituents independently selected from the group halogen, hydroxy, and —$NR^AR^B$;

wherein $R^A$ and $R^B$ are substituents independently selected from hydrogen or $C_{1-6}$alkyl;

R² is one to two substituents independently selected from the group consisting of hydrogen, $C_{1-4}$alkyl, $C_{2-6}$alkenyl, $C_{2-6}$alkynyl, $C_{1-4}$alkoxy, —NR$^C$R$^D$, hydroxy, and halogen;
  wherein alkyl, alkenyl, alkynyl, and alkoxy are optionally substituted on a terminal carbon with one to three substituents independently selected from the group halogen, hydroxy, $C_{1-4}$alkoxy, and —NR$^C$R$^D$;
  wherein R$^C$ and R$^D$ are substituents independently selected from hydrogen or $C_{1-6}$alkyl; R$^C$ and R$^D$ are optionally taken together with the atoms to which they are attached to form a five to seven membered monocyclic ring;
Z is selected from the group consisting of —CH$_2$— and —CH—;
A is selected from the group consisting of aryl, —CH(CH$_2$)$_{1-3}$—, and —(CH$_2$)$_{1-3}$—; provided that when A is —CH(CH$_2$)$_{1-2}$— and Z is —CH— then a double bond is formed between A and Z;
B is —NH— when optionally present;
m and n are integers from 1 to 3;
X is selected from the group consisting of O, S, and two hydrogen atoms;
U is independently selected from the group consisting of —CH—, N, and S, provided that no more than one U represents S or N; and that U can only be S when W is not present;
W is selected from the group consisting of —CH— and N when optionally present;
and enantiomers, diastereomers, tautomers, or pharmaceutically acceptable salts thereof.

2. The compound of claim 1 wherein R$^1$ is selected from the group consisting of hydrogen, $C_{1-4}$alkoxy, —NR$^A$R$^B$, and hydroxy.

3. The compound of claim 1 wherein R$^1$ is selected from the group consisting of hydrogen and hydroxy.

4. The compound of claim 1 wherein R$^2$ is selected from the group consisting of hydrogen, $C_{1-4}$alkyl, $C_{1-4}$alkoxy, and halogen.

5. The compound of claim 1 wherein R$^2$ is selected from the group consisting of hydrogen, fluorine, and $C_{1-4}$alkoxy.

6. The compound of claim 1 wherein Z is selected from the group consisting of —CH$_2$— and —CH—; provided that Z is —CH— only when A is —CH(CH$_2$)$_{1-2}$—, and taken together to form a double bond between A and Z.

7. The compound of claim 1 wherein Z is —CH$_2$—.

8. The compound of claim 1 wherein A is selected from the group consisting of aryl, —CH(CH$_2$)$_{1-2}$—, and —(CH$_2$)$_{1-3}$—; provided that A is —CH(CH$_2$)$_{1-2}$— only when Z is —CH—, taken together to form a double bond between A and Z.

9. The compound of claim 1 wherein A is selected from the group consisting of aryl and —(CH$_2$)$_{1-2}$.

10. The compound of claim 1 wherein A is selected from the group consisting of phenyl or —(CH$_2$)$_{1-2}$.

11. The compound of claim 1 wherein B is —NH—.

12. The compound of claim 1 wherein m and n are integers from 1 to 2, but are not both 2 in the same instance.

13. The compound of claim 1 wherein R is selected from the group consisting of 1,4,5,6-tetrahydro-pyrimidin-2-yl, pyridin-2-yl, and 5,6,7,8-tetrahydro-[1,8]naphthyridin-2-yl.

14. The compound of claim 1 wherein R is selected from the group consisting of 1,4,5,6-tetrahydropyrimidin-2-yl and 4-(5,6,7,8-tetrahydro-[1,8]naphthyridin-2-yl.

15. The compound of claim 1 wherein X is selected from the group consisting of O and S.

16. The compound of claim 1 wherein X is O.

17. The compound of claim 1 wherein U is selected from the group consisting of —CH—, N and S, provided that no more than one U represents S or N; and provided that U can only be S when W is not present.

18. The compound of claim 1 wherein U is —CH—.

19. The compound of claim 1 wherein W is present and selected from the group consisting of —CH— and N.

20. The compound of claim 1 wherein W is present and is —CH—.

21. Compounds of Formula (II):

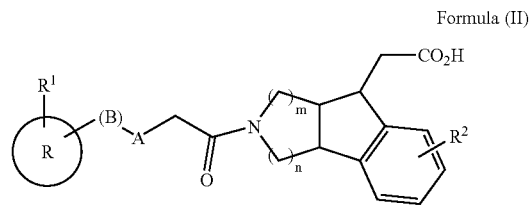

Formula (II)

wherein R, R$^1$, B, A, m, n, and R$^2$ are dependently selected from the group consisting of:

| Cpd | Stereo chem. | R | R$^1$ | B | A | m | n | R$^2$ |
|---|---|---|---|---|---|---|---|---|
| 1 | cis | 1,4,5,6,-tetrahydro-pyrimidin-2-yl | H | NH | 1,3-phenyl | 2 | 1 | H |
| 2 | trans | 1,4,5,6,-tetrahydro-pyrimidin-2-yl | H | NH | 1,3-phenyl | 2 | 1 | H |
| 3 | racemic | 5,6,7,8-tetrahydro-[1,8]naphthyridine-2-yl | H | absent | —(CH$_2$)$_2$— | 2 | 1 | H |
| 4 | racemic | 5,6,7,8-tetrahydro-[1,8]naphthyridine-2-yl | H | absent | —(CH$_2$)— | 2 | 1 | H |
| 5 | racemic | 1,4,5,6,-tetrahydro-pyrimidin-2-yl | OH | NH | 1,3-phenyl | 2 | 1 | H |
| 6 | cis | Pyridin-2-yl | H | NH | —(CH$_2$)$_2$— | 2 | 1 | H |

| Cpd | Stereo chem. | R | R¹ | B | A | m | n | R² |
|---|---|---|---|---|---|---|---|---|
| 7 | trans | Pyridin-2-yl | H | NH | —(CH₂)₂— | 2 | 1 | H |
| 8 | racemic | Pyridin-2-yl | H | NH | —(CH₂)₃— | 2 | 1 | H |
| 9 | cis | 5,6,7,8-tetrahydro-[1,8]naphthyridine-2-yl | H | absent | —(CH₂)₂— | 1 | 2 | H |
| 10 | trans | 5,6,7,8-tetrahydro-[1,8]naphthyridine-2-yl | H | absent | —(CH₂)₂— | 1 | 2 | H |
| 11 | racemic | 5,6,7,8-tetrahydro-[1,8]naphthyridine-2-yl | H | absent | —(CH₂)— | 1 | 2 | H |
| 12 | racemic | 5,6,7,8-tetrahydro-[1,8]naphthyridine-2-yl | H | absent | —(CH₂)— | 1 | 1 | H |
| 13 | cis | 5,6,7,8-tetrahydro-[1,8]naphthyridine-2-yl | H | absent | —(CH₂)— | 1 | 1 | H |
| 14 | trans | 5,6,7,8-tetrahydro-[1,8]naphthyridine-2-yl | H | absent | —(CH₂)— | 1 | 1 | H |
| 15 | racemic | 5,6,7,8-tetrahydro-[1,8]naphthyridine-2-yl | H | absent | —(CH₂)₂— | 1 | 1 | H |
| 16 | racemic | 5,6,7,8-tetrahydro-[1,8]naphthyridine-2-yl | H | absent | —(CH₂)— | 1 | 1 | F |

22. The compound of Formula (II):

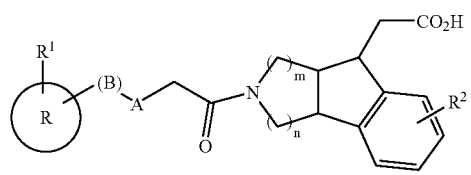

Formula (II)

The compound of Formula (II) wherein R, R¹, B, A, m, n, and R² are dependently selected from the group consisting of:

| Cpd | Stereo chem. | R | R¹ | B | A | m | n | R² |
|---|---|---|---|---|---|---|---|---|
| 1 | cis | 1,4,5,6,-tetrahydro-pyrimidin-2-yl | H | NH | 1,3-phenyl | 2 | 1 | H |
| 2 | trans | 1,4,5,6,-tetrahydro-pyrimidin-2-yl | H | NH | 1,3-phenyl | 2 | 1 | H |
| 3 | racemic | 5,6,7,8-tetrahydro-[1,8]naphthyridine-2-yl | H | absent | —(CH₂)₂— | 2 | 1 | H |
| 4 | racemic | 5,6,7,8-tetrahydro-[1,8]naphthyridine-2-yl | H | absent | —(CH₂)— | 2 | 1 | H |
| 12 | racemic | 5,6,7,8-tetrahydro-[1,8]naphthyridine-2-yl | H | absent | —(CH₂)— | 1 | 1 | H |
| 13 | cis | 5,6,7,8-tetrahydro-[1,8]naphthyridine-2-yl | H | absent | —(CH₂)— | 1 | 1 | H |
| 14 | trans | 5,6,7,8-tetrahydro-[1,8]naphthyridine-2-yl | H | absent | —(CH₂)— | 1 | 1 | H |
| 15 | racemic | 5,6,7,8-tetrahydro-[1,8]naphthyridine-2-yl | H | absent | —(CH₂)₂— | 1 | 1 | H |
| 16 | racemic | 5,6,7,8-tetrahydro-[1,8]naphthyridine-2-yl | H | absent | —(CH₂)— | 1 | 1 | F |

23. A composition comprising the compound of claim 1 and a pharmaceutically acceptable carrier.

24. A method for treating or ameliorating an αv integrin mediated disorder selected from the group consisting of diabetic retinopathy, macular degeneration, osteoporosis, and rheumatoid arthritis in a subject in need thereof comprising administering to the subject a therapeutically effective amount of the compound of claim 1.

25. The method of claim 24 wherein the therapeutically effective amount of the compound of claim 1 is from about 0.001 mg/kg/day to about 1000 mg/kg/day.

26. The method of claim 24 wherein the αv integrin mediated disorder is rheumatoid arthritis.

27. The method of claim 24 wherein the αv integrin mediated disorder is osteoporosis.

28. The method of claim 24 wherein the αv integrin mediated disorder is macular degeneration.

29. The method of claim 24 wherein the αv integrin mediated disorder is diabetic retinopathy.

* * * * *